US008362007B1

(12) United States Patent
Mash et al.

(10) Patent No.: US 8,362,007 B1
(45) Date of Patent: Jan. 29, 2013

(54) SUBSTITUTED NORIBOGAINE

(75) Inventors: Deborah C. Mash, Miami, FL (US);
Richard D. Gless, Jr., Oakland, CA (US); Robert M. Moriarty, Michiana Shores, IN (US)

(73) Assignee: Demerx, Inc., Miami, FL (US)

( * ) Notice: Subject to any disclaimer, the term of this patent is extended or adjusted under 35 U.S.C. 154(b) by 0 days.

(21) Appl. No.: 13/104,410

(22) Filed: May 10, 2011

Related U.S. Application Data

(60) Provisional application No. 61/419,776, filed on Dec. 3, 2010, provisional application No. 61/333,668, filed on May 11, 2010.

(51) Int. Cl.
*A61P 25/00* (2006.01)
*A61K 31/55* (2006.01)
*C07D 487/18* (2006.01)

(52) U.S. Cl. .................. 514/214.02; 540/579
(58) Field of Classification Search ............. 514/214.02; 540/579
See application file for complete search history.

(56) References Cited

U.S. PATENT DOCUMENTS

| | | | |
|---|---|---|---|
| 2,813,873 A | 11/1957 | Janot et al. | |
| 3,516,989 A | 6/1970 | Sallay | |
| 3,557,126 A * | 1/1971 | Sallay ..................... | 540/579 |
| 3,574,220 A | 4/1971 | Sallay | |
| 3,639,408 A | 2/1972 | Nagata et al. | |
| 3,715,361 A | 2/1973 | Epstein et al. | |
| 3,875,011 A | 4/1975 | Rubenstein et al. | |
| 4,107,288 A | 8/1978 | Oppenheim et al. | |
| 4,272,541 A | 6/1981 | Kotick et al. | |
| 4,375,414 A | 3/1983 | Strahilevitz | |
| 4,444,758 A | 4/1984 | Scherschlicht et al. | |
| 4,462,941 A | 7/1984 | Lee et al. | |
| 4,464,378 A | 8/1984 | Hussain | |
| 4,499,096 A | 2/1985 | Lotsof | |
| 4,573,995 A | 3/1986 | Chen et al. | |
| 4,587,243 A | 5/1986 | Lotsof | |
| 4,604,365 A | 8/1986 | O'Neill et al. | |
| 4,620,977 A | 11/1986 | Strahilevitz | |
| 4,626,539 A | 12/1986 | Aungst et al. | |
| 4,661,492 A | 4/1987 | Lewis et al. | |
| 4,668,232 A | 5/1987 | Cordes et al. | |
| 4,806,341 A | 2/1989 | Chien et al. | |
| 4,857,523 A | 8/1989 | Lotsof | |
| 5,026,697 A | 6/1991 | Lotsof | |
| 5,075,341 A | 12/1991 | Mendelson et al. | |
| 5,145,684 A | 9/1992 | Liversidge et al. | |
| 5,149,538 A | 9/1992 | Granger et al. | |
| 5,152,994 A | 10/1992 | Lotsof | |
| 5,283,247 A | 2/1994 | Dwivedi et al. | |
| 5,290,784 A | 3/1994 | Qu et al. | |
| 5,316,759 A | 5/1994 | Rose et al. | |
| 5,382,657 A | 1/1995 | Karasiewicz et al. | |
| 5,426,112 A | 6/1995 | Zagon et al. | |
| 5,552,406 A | 9/1996 | Mendelson et al. | |
| 5,574,052 A | 11/1996 | Rose et al. | |
| 5,578,645 A | 11/1996 | Askanazi et al. | |
| 5,580,876 A | 12/1996 | Crain et al. | |
| 5,591,738 A | 1/1997 | Lotsof | |
| 5,618,555 A | 4/1997 | Tokuda et al. | |
| 5,703,101 A | 12/1997 | Rose et al. | |
| 5,726,190 A | 3/1998 | Rose et al. | |
| 5,760,044 A | 6/1998 | Archer | |
| 5,861,422 A | 1/1999 | Rose et al. | |
| 5,865,444 A | 2/1999 | Kempf et al. | |
| 5,925,634 A | 7/1999 | Olney | |
| 5,935,975 A | 8/1999 | Rose et al. | |
| 6,211,360 B1 | 4/2001 | Glick et al. | |
| 6,291,675 B1 | 9/2001 | Coop et al. | |
| 6,348,456 B1 | 2/2002 | Mash et al. | |
| 6,451,806 B2 | 9/2002 | Farrar | |
| 6,806,291 B1 | 10/2004 | Sunkel et al. | |
| 6,864,271 B2 | 3/2005 | Bazan et al. | |
| 7,220,737 B1 * | 5/2007 | Mash ..................... | 514/214.03 |
| 7,754,710 B2 * | 7/2010 | Mash ..................... | 514/214.02 |
| 8,178,524 B2 | 5/2012 | Mash | |
| 2003/0153552 A1 * | 8/2003 | Mash et al. ............. | 514/214.03 |
| 2006/0051317 A1 | 3/2006 | Batrakova et al. | |
| 2010/0311722 A1 | 12/2010 | Mash | |
| 2010/0311723 A1 | 12/2010 | Mash | |
| 2010/0311725 A1 | 12/2010 | Mash | |
| 2012/0083485 A1 | 4/2012 | Mash | |

FOREIGN PATENT DOCUMENTS

| | | |
|---|---|---|
| CA | 2039197 | 9/1995 |
| DE | 22 17 132 | 10/1972 |
| GB | 0 841 697 | 7/1960 |
| GB | 0 924 042 | 4/1963 |
| GB | 1 256 914 | 12/1971 |
| GB | 1 378 348 | 12/1974 |
| GB | 2 271 059 | 4/1994 |
| JP | 04-221315 | 8/1992 |
| WO | WO-91/18609 A1 | 12/1991 |
| WO | WO-93/20825 A1 | 10/1993 |
| WO | WO-93/25217 A1 | 12/1993 |
| WO | WO-94/06426 A1 | 3/1994 |
| WO | WO-94/14490 A1 | 7/1994 |
| WO | WO-96/03127 A1 | 2/1996 |

OTHER PUBLICATIONS

Mulamba et al., Alkaloids from *Tabernanthe pubescens*, Journal of Natural Products, vol. 44, No. 2, pp. 184-189, 1981.*
U.S. Appl. No. 13/104,406, filed May 10, 2011, Mash et al.
U.S. Appl. No. 13/165,626, filed Jun. 21, 2011, Mash, Deborah C.
U.S. Appl. No. 13/165,639, filed Jun. 21, 2011, Mash et al.
U.S. Appl. No. 13/165,642, filed Jun. 21, 2011, Mash et al.
U.S. Appl. No. 13/198,593, filed Nov. 7, 2011, Mash et al.
U.S. Appl. No. 13/383,405, Moriarty, Robert.
U.S. Appl. No. 13/496,185, Mash, Deborah C.
Ala-Hurula et al. "Erogotamine Abuse: Results of Ergotamine Discontinuation, with Special Reference to the Plasma Concentrations", Cephalalgia, 2/4: abstract only, 1982.
Ala-Hurula et al. "Tolfenamic Acid and Ergotamine Abuse", Headache: The Journal of Head and Face Pain, 21(6): abstract only, 1981.
Alexander. "A Procedure for Drug Screening Without the Need to Transport Urines Use of Ion Exchange Papers and Hem Agglutination Inhibition", Clin Toxicol, 9(3): abstract only, 1976.
Alim et al. "Open-Label, Dose Run-Up Study of Diethylpropion in Initial Cocaine Abstinence", Clinical Neuropharmacology, 17(2): abstract only, 1994.
Almeida. "Use and Abuse of Alcohol and Drugs a Clinical Study of Certain Aspects of Their Interrelationship", Bol of Sanit Panam, 88(1), abstract only, 1980.

(Continued)

*Primary Examiner* — Brenda Coleman
(74) *Attorney, Agent, or Firm* — Foley & Lardner LLP

(57) ABSTRACT

This invention relates noribogaine derivatives, compositions and methods of use thereof.

15 Claims, No Drawings

OTHER PUBLICATIONS

Al-Shabanah et al. "Gastric Antiulcer and Cytoprotective Effects of Cathinone, a Psychoactive Alkaloid of Khat (Catha Edulis Forsk.) and Amphetamine in Rats", Regulatory Peptides, abstract only, 1994.
Azevedo et al. "Adrenergic Nerve Degeneration Induced by Condensation Products of Adrenaline and Acetaldehyde", Naunyn-Schmiedeberg's Arch Pharmacol, 300(2): abstract only, 1977.
Bagal et al. "Modulation of Morphine-Induced Antinociception by Ibogaine and Noribogaine", Brain Research, 741(1-2): pp. 258-262, 1996.
Ban. "Adverse Effects to Psychotomimetics. Proposition of a Psychopharmacological Classification", In: Radouco-Thomas S, ed. Pharmacologie, Toxicologie, et abus des psychotomimetiques (hallucinogens)., QV 109: abstract only, 1974.
Bartlett et al. "The Alkaloids of Tabernanthe iboga. Part IV..sup.1 The Structures of Ibogamine, Ibogaine, Tabernanthine and Voacangine", J. Am. Chem. Soc., 80: pp. 126-136, 1958.
Batrakova. "Pluronic P85 Enhances the Delivery of Digoxin to the Brain: in Vitro and in Vivo Studies", The J. of Pharm. and Exp. Thera, 296, p. 551-557, 2001.
Beaubrun. "The Diagnosis and Management of Acute Psychotic Reaction Due to Alcohol and Drugs", Caribb Med J, 36(1): abstract only, 1975.
Beck et al. "Energy-Dependent Reduced Drug Binding as a Mechanism of Vinca Alkaloid Resistance in Human Leukemic Lymphoblasts", Mol Pharmacol, 24(3): abstract only, 1983.
Benet et al. "Pharmacokinetics: Biotransformation of Drugs." in Gilman et al. Goodman and Gilman's the Pharmacological Basis of Therapeutics (1990) :13-16.
Benoist et al. "Comparative Effects of Fagaronine Adriamycin and Aclacinomycin on K562 Cell Sensitivity to Natural-Killer-Mediated Lysis Lack of Agreement Between Alteration of Transferrin Receptor and CD15 Antigen Expressions and Induction of Resistance to Natural Killer", Cancer Immunol Immunother, 30(5): abstract only, 1989.
Bert et al. "Non-Amphetaminic Central Stimulation by Alkaloids from the Ibogaine and Vobasine Series", Planta Med., 54(3): abstract only, 1988.
Bhargava et al. "Effects of ibogaine and noribogaine on the antinociceptive action of mu-, delta- and kappa-opioid receptor agonists in mice", Brain Research 752:234-238, 1997.
Blum et al. "Peyote a Potential Ethnopharmacologic Agent for Alcoholism and Other Drug Dependencies Possible Biochemical Rationale", Clin Toxicol, 11(4): abstract only, 1977.
Blum et al. "Possible Role of Tetrahydroisoquinoline Alkaloids in Postalcohol Intoxication States", Ann N Y Acad Sci, 273: abstract only, 1976.
Blum et al. "Putative Role of Isoquinoline Alkaloids in Alcoholism: A Link to Opiates", Alcohol Clin Exp Res, 2(2): abstract only, 1978.
Brady et al. "Analgesic Effects of Intraventricular Morphine and Enkephalins in Nondependent and Morphine-Dependent Rats", J. Pharmacol. Exp. Ther., 222(1): abstract only, 1982.
Buchi et al. "The total synthesis of iboga alkaloids", J. Am. Chem. Soc. vol. 88, p. 3099-3109, 1966.
Bundgaard. "Design of Prodrugs: Bioreversible Derivatives for Various Functional Groups and Chemical Entities." Design of Prodrugs, 1-10, 1985.
Bussel et al. "Isolated Thrombocytopenia in Patients Infected with HIV Treatment with Intravenous Gamma Globulin", Am J Hematol, 28(2): abstract only, 1988.
Caldwell et al. "The Biochemical Pharmacology of Abused Drugs. III. Cannabis, Opiates, and Synthetic Narcotics", Clin. Pharmacol. Ther., 16/6: abstract only, 1974.
Cankat. "Pharmacological Aspects of Drug Induced Headache", Funct. Neurol., 7/6: abstract only, 1992.
Cappendijk et al. "Inhibitory Effects of Ibogaine on Cocaine Self-Administration in Rats", Eur. J. Pharmacol., 241 (2-3): abstract only, 1993.
Cappendijk et al. "The Inhibitory Effect of Norharman on Morphine Withdrawal Syndrome in Rats: Comparisons with Ibogaine", Behavioural Brain Research, pp. 1-3, 1994.
Chemical abstract, RN 16671-16-2 Registry, 1967.
Chemical abstract, RN 3464-63-9 Registry, 1965.
Chemical abstract, RN 481-87-8 Registry, 1952.
Chemical abstract, RN 4865-78-5 Registry. 1965.
Chemical abstract, RN 53508-36-4 Registry, 1974.
Chemical abstract, RN 57511-56-5 Registry, 1975.
Chemical abstract, RN 77123-15-0 Registry, 1980.
Chemical abstract, RN 83-74-9 Registry, 1934.
Chemical abstract, RN 88660-07-5 Registry, 1983.
Chemical abstract, RN 88660-09-7 Registry, 1983.
Cherny et al. "Opioid responsiveness of cancer pain syndromes caused by neuropathic or nociceptive mechanisms: a combined analysis of controlled, single-dose studies", Neurobiology 44:857-861, 1994.
Cheze et al. "Determination of ibogaine and noribogaine in biological fluids and hair by LC-MS/MS after *Tabernanthe iboga* abuse", Forensic Science International, Elsevier Scientific Publishers Ireland Ltd, IE, vol. 176. No. 1, pp. 58-66, 2007.
Criel et al. "Drug Dependent Red Cell Antibodies and Intravascular Haemolysis Occurring in Patients Treated with 9 Hydroxy-Methyl-Ellipticinium", Br J Haematol, 46(4): abstract only, 1980.
Damstrup et al. "Retroperitoneal Fibrosis After Long-Term Daily Use of Ergotamine", Int. Urol. Nephrol., 18/3: abstract only, 1986.
Deecher et al. "Mechanisms of Action of Ibogaine and Harmaline Congeners Based on Radioligand Binding Studies", Brain Research, 571(2): pp. 242-247, 1992.
Diener et al. "Analgesic-Induced Chronic Headache Long-Term Results of Withdrawal Therapy", J Neurol, 236(1): abstract only, 1989.
Dierckx et al. "Intraarterial Sodium Nitroprusside Infusion in the Treatment of Severe Ergotism", Clin. Neuropharmacol., 9/6: abstract only, 1986.
Dzoljic et al. "Effect of Ibogaine on Naloxone-Precipitated Withdrawal Syndrome in Chronic Morphine-Dependent Rats", Arch. Int. Pharmacodyn., 294:64-70, 1988.
Eberwine et al. "Molecular Analysis of Cellular Responses to Opiate Use", Fidia Res. Found. Symp. Ser., 7(Neurotransm. Regul. Gene Transcr.): abstract only, 1991.
Elkind. "Drug Abuse and Headache", Med Clin North Am, 75(3): abstract only, 1991.
Evenson. "Developments in Therapeutic Drug Monitoring and Alkaloid Analysis", Fed Proc, 34(12): abstract only, 1975.
Faglia et al. "Dihydroergocryptine in Management of Microprolactinomas", J Clin Endocrinol Metab, 65(4): abstract only, 1987.
Fairchild et al. "Keynote Address: Multidrug Resistance: A Pleiotropic Response to Cytotoxic Drugs", Int. J. Radiat. Oncol. Biol. Phys., 20/2: abstract only, 1991.
Finkle. "Phencyclidine Identification by Thin-Layer Chromatography. A Rapid Screening Procedure for Emergency Toxicology", Am. J. Clin. Pathol., 70/2: abstract only, 1978.
Fonne-Pfister et al. "Xenobiotic and Endobiotic Inhibitors of Cytochrome P-450dbl Function, the Target of the Debrisoquine / Sparteine Type Polymorphism", Biochem. Pharmacol., 37(20): abstract only, 1988.
Frances et al. "Effects of Ibogaine on Naloxone-Precipitated Withdrawal in Morphine-Dependent Mice", Fundam Clin Pharmacol, 6(8-9): abstract only, 1992.
Gabr et al. "Changes in Absolute Amount of Alkaloids in Datura-Metel Treated with Certain Growth Regulators", Herba Pol, 21(2): abstract only, 1975.
Garcia et al. "Chronic pain states: pathophysiology and medical therapy", Seminars in Arthritis and Rheumatism, 27:1-16, 1997.
Gennaro. "Remington: The Science and Practice of Pharmacy", Mack Publishing Col., vol. II, pp. 1736 & 1814, 1995.
George et al. "Palliative medicine", Postgrad. Med. Journal, vol. 69, pp. 426-449, 1993.
Gifford et al. "Effect of Chronic Cocaine Treatment on D SUB 2 Receptors Regulating the Release of Dopamine and Acetylcholine in the Nucleus Accumbens and Striatum", Pharmacology, Biochemistry and Behavior, 41(4): abstract only, 1992.
Glick et al. "Effects of iboga Alkaloids on Morphine and Cocaine Self-Administration in Rats: Relationship to Tremorigenic Effects and to Effects on Dopamine Release in Nucleus Accumbens and Striatum." Brain Research, 657:14-22, 1994.

Glick et al. "Effect of Ibogaine on Acute Signs of Morphine Withdrawal in Rats: Independence from Tremor", Neuropharmacology, 31/5: abstract only, 1992.

Glick et al. "Effects of Aftereffects of Ibogaine on Morphine Self-Administration in Rats", European Journal of Pharmacology, 195(3): abstract only, 1991.

Glick et al. "Ibogaine-like effects of noribogaine in rats", Brain Research, 713:294-297, 1996.

Glick et al. "Local Effects of Ibogaine on Extracellular Levels of Dopamine and Its Metabolites in Nucleus Accumbens and Striatum: Interactions with D-Amphetamine", Brain Research, 628(1-2): abstract, 1993.

Gold et al. "Effect of Methadone Dosage on Clonidine Detoxification Efficacy", Am. J. Psychiatry, 137/3: abstract only, 1980.

Gothoni. "Harmine-, Lon-954- and 5-Hydroxytryptophan-Induced Tremors in Rats Withdrawn from Ethanol", Acta Pharmacol Toxicol, 57(1): abstract only, 1985.

Gross. "Effect of Ergot Alkaloids on Serum Prolactin in Non-Psychotic Organic Brain Syndrome of the Elderly", Exp Aging Res, 5(4): abstract only, 1979.

Gunn. "Relations Between Chemical Constitution, Pharmacological Actions, and Therapeutic Uses, in the Harmine Group of Alkaloids", From the Pharmacological Laboratory, University of Oxford:379-396, 1935.

Haber et al. "Tetrahydroisoquinolines—Endogenous Products After Chronic Alcohol Abuse", Pharmazie, 47/1: abstract only, 1992.

Halikas et al. "Treatment of Crack Cocaine Use with Carbamazepine", Am J Drug Alcohol Abuse, 18(1): abstract only, 1992.

Hanks. "Opioid-responsive and opioid-non-responsive pain in cancer", British Medical Bulletin 47:718-731, 1991.

Hardman et al. "Goodman & Gilman's The Parmacological Basis of Therapeutics" (9th ed, 1996) p. 51 and 57-58.

Harsing, Jr. et al. "Evidence that Ibogaine Releases Dopamine from the Cytoplasmic Pool in Isloated Mouse Striatum", Journal of Neural Transmission General Section, 96(3): abstract only, 1994.

Hearn et al. "Identification and Quantitation of Ibogaine and an o-Demethylated Metabolite in Brain and Biological Fluids Using Gas Chromatography-Mass Spectrometry." J. Analytical Toxicology, 19:427-434, 1995.

Heel et al. "Buprenorphine: A Review of Its Pharmacological Properties and Therapeutic Efficacy", Drugs, 17(2): abstract only, 1979.

Henry et al. "Reversible Cerebral Arteriopathy Associated with the Administration of Ergot Derivatives", Cephalalgia, 4/3: abstract only, 1984.

Ho et al. "Metabolism of Harmaline in Rats." Biochemical Pharmacology, 20:1313-1319, 1971.

Hoes. "Clinical Criteria for the Selection of Anxiolytics", Tijdschr. Ther. Geneesm. Onderz., 9/9: abstract only, 1984.

Holbrook. "Nicotine Addiction." in Isselbacher et al. Harrison's Principles of Internal Medicine:2433-2437, 1994.

Holzner et al. "The Neuroleptic Sleeping Course in Chronic Headache", Therapiewoche, 35/36: abstract only, 1985.

Huang et al. "Cytotoxicity and Sister Chromatid Exchanges Induced in Vitro by Six Anticancer Drugs Developed in the People's Republic of China", J Natl Cancer Inst, 71(4): abstract only, 1983.

Hubens et al. "Chronic Intake of a Hydrogenated Ergot Alkaloid Causing Peripheral Vascular Ischemia—A Case Report", Vasc. Surg., 21/4: abstract only, 1987.

Huffman et al. "A Formal Synthesis of (±)-Ibogamine", J. Org. Chem. vol. 50, pp. 1460-1464, 1985.

Isler. "Treatment of Headache", Schweiz. Med. Wochenschr., 114/35: abstract only, 1984.

Jaffe. "Drug Addiction and Drug Abuse." In Gilman et al. Goodman and Gilman's The Pharmacological Basis of Therpeutics:522-523, 559-568, 1990.

Jaffe. "Psychopharmacology and Opiate Dependence", U.S. Public Health Serv. Publ., 1957-1967:1836, 1967.

James, "Linkers for solid phase organic synthesis", Tetrahedron 55, 4855-4946, 1999.

Jane et al. "High-Performance Liquid Chromatographic Analysis of Basic Drugs on Silica Columns Using Non-Aqueous Ionic Eluents. II. Application of UV, Fluorescence and Electrochemical Oxidation detection", J. Chromatogr., 323(2): abstract only, 1985.

Jansen et al. "Ethnopharmacology of Kratom and the Mitragyna Alkaloids", J Ethnopharmacol, 23(1): abstract only, 1988.

Janzen. "History of Use of Psychotropic Drugs in Central Africa", Psychotropes, 1/2: abstract only, 1983.

Justins. "Management strategies for chronic pain", Annals of the Rheumatic Diseases, vol. 55, pp. 588-596, 1996.

Kalix. "Khat: A Plant with Amphetamine Effects", J Subst Abuse Treat, 5(3): abstract only, 1988.

Kalix. "Pharmacological Properties of the Stimulant Khat", Pharmacol. Ther., 48/3: abstract only, 1990.

Keefner. "A Gas Chromatography—Mass Spectrometry (GCMS) Method for Ibogaine", Society for Neuroscience Abstracts, 19(1-3): abstract only, 1993.

Keller et al. "Modulation of Neopterin Release by Human Kupffer Cells in Culture: Possible Implication in Clinical Monitoring of HIV-Seropositive Subjects", Cells Hepatic Sinusoid, 3: abstract only, 1991.

Knoll. "Azidomorphines and Homopyrimidazols: A New Approach to the Ideal Analgetic", Acta Physicol Pharmacol Bulg, 3(2): abstract only, 1977.

Knoll. "Azidomorphines: A New Family of Potent Analgesics with Low Dependence Capacity", Prog. Neuro-Psychopharmacol., 3/1-3: abstract only, 1979.

Koch et al. "Drug-Induced Liver Injury in Liver Biopsies of the Years 1981 and 1983, their Prevalence and Type of Presentation", Path. Res. Pract., 179: abstract only, 1985.

Konig. "Psychiatric Intensive Therapy After Acute Alkaloid Withdrawal Syndrome", Infusionsther Klin Ernahr, 6(1): abstract only, 1979.

Kornetsky, "Pharmacology Drugs Affecting Behavior", New York, John Wiley & Sons, pp. 186-187, 1976.

Kostowski et al. "The Effects of Some Hallucinogens on Aggressiveness of Mice and Rats" Pharmacology vol. 7, pp. 259-63, 1972.

Krug. "Cocaine Abuse: Historical, Epidemiologic, and Clinical Perspectives for Pediatricians", Advances in Pediatrics, 36:369-406, 1989.

Kupers et al., "Morphine differentially affects the sensory and affective pain ratings in neuorgenic and idiopathic forms of pain." Pain 47:5-12, 1991.

Lakoski et al. "Electrophysiologic Characterization of an Ibogaine Metabolite in Dorsal Raphe Nucleus and Hippocampus." Soc. Neurosc. 21:716 Abstract only, 1995.

Larson-Prior et al. "Electrophysiologic Characterization of an Ibogaine Metabolite in the Cerebellar Cortex." Soc. Neurosc. 21:716 Abstract only, 1995.

Lemontt et al. "Increase MDR Gene Expression and Decreased Drug Accumulation in Multidrug-Resistant Human Melanoma Cells", Cancer Res, 48(22): abstract only, 1988.

Leoni et al. "Effect of Cocaine and Morphine on Neutral Endopeptidase Activity of Human Peripheral Blood Mononuclear Cells Cultures with Lectins", Cell Biochem Funct, 11(3): abstract only, 1993.

Lerida et al. "Incidence of Morphine Withdrawal and Quasi-Abstinence Syndrome in a Model of Chronic Pain in the Rat", Neurosci., 81(1-2): abstract only, 1987.

Lewis et al. "Adverse Reactions and Interactions with .beta.-Adrenoceptor Blocking Drugs", Med. Toxicol., 1/5: abstract only, 1986.

Lewis et al. "Narcotic Analgesics and Antagonists", Annu Rev Pharmacol, 11: abstract only, 1971.

Licht et al. "Induction of Multiple-Drug Resistance During Anti-Neoplastic Chemotherapy In-Vitro", Int J Cancer, 49(4): abstract only, 1991.

Ling et al., "Drugs of Abuse-Opiates", in Addtiction Medicine [Special Issue], Western Journal of Medicine, 152:565-572, 1990.

Low et al. "Effects of Acronycine and Cytouchalasin B on the Division of Rat Leukemia Cells", Exp Cell Res, 131(1): abstract only, 1981.

Ma et al. "Inhibition of Respiratory Burst Activity in Alveolar Macrophages by Bisbenzylisoquinoline Alkaloids: Characterization of Drug-Cell Interaction", Exp. Lung Res., 18/6: abstract only, 1992.

Maisonneuve et al. "Interactions of Ibogaine and D-Amphetamine: in vivio Microdialysis and Motor Behavior in Rats." Brain Research 579:87-92, 1992.

Maisonneuve et al. "Acute and Prolonged Effects of Ibogaine on Brain Dopamine Metabolism and Morphine-Induced Locomotor Activity in Rats", Brain Research, 575(1): abstract only, 1992.

Maisonneuve et al. "Interactions Between Ibogaine, a Potential Anti-Addictive Agent, and Morphine: an in Vivo Microdialysis Study", Eur. J. Pharmacol., 199(1): abstract only, 1991.

Martellotta et al. "Effects of the Calcium Antagonist Isradipine on Cocaine Intravenous Self-Administration in Rats", Psychopharmacologia, 113(3-4): Abstract only, 1994.

Martin et al. "Neuropathic Pain in Cancer Patients: Mechanisms, Syndromes, and Clinical Controversies," Journal of Pain and Symptom Management 14(2):99-117, 1997.

Mash et al, "Properties of Ibogaine and its Principle Metabolite (12-hydroxyibogamine) at the MK-801 binding site of the NMDA receptor complex," Neuroscience Letters, 192, 53-56, 1995.

Mash et al. "Ligand Binding Profiles of Ibogaine and its O-demethylated Metabolite Noribogaine: Implications for Developing Novel Multi-target Anti-addiction Agents." Soc. Neurosc. (1995) 21:717 Abstract only.

Mash et al. "Preclinical screening of an ibogaie metabolite (noribogaine) on cocaine-induced hyperlocomotion and cocaine self-administration." Soc. Neurosc. 22:1929 Abstract only, 1996.

Mash et al. "Ibogaine in the Treatment of Heroin Withdrawal," The Alkaloids 56:1-17, 2001.

Mateer et al. "Reversible Ipecac Myopathy", Arch. Neurol., 42/2: abstract only, 1985.

Matharu et al. "Preformulation and Development of Ibogaine Injection for the Treatment of Drug Abuse", Pharmaceutical Research, 10: abstract only, 1993.

Mattingly et al. "Selective Antagonism of Dopamine D Sub1 and D Sub 2 Receptors Does Not Block the Development of Behavioral Sensitization to Cocaine", Psychopharmacologia, 114(2): abstract only, 1994.

McNeish et al. "The 5-HT Sub 3 Antagonist Zacopride Attenuates Cocaine-Induced Increases in Extracellular Dopamine in Rat Nucleus Accumbens", Pharmacology, Biochemistry, and Behavior, 45(4): abstract only, 1993.

Melchior et al. "Preference for Alcohol Evoked by Tetra Hydro Papaveroline Chronically Infused in the Cerebral Ventricle of the Rat", Pharmacol Biochem Behav, 7(1): abstract only, 1977.

Mendelson et al. "Cocaine and Other Commonly Abused Drugs." in Isselbacher et al. Harrison's Principles of Internal Medicine:2429-2433, 1994.

Menzies et al. "Gangrene of the Small Bowel: A Complication of Methysergide Therapy", Aust. N. Z. J. Surg., 52/5: abstract only, 1982.

Metelitsa. "Pharmacological Agents in Controlling Smoking", Biull Vsesoiuznogo Kardiol Nauchn Tsentra, 10(1): abstract only, 1987.

Millan, "k-Opioid Receptors and Analgesia," Trendes in Pharmacologicla Sciences, 11, pp. 70-76, 1990.

Mizuhashi et al. "Antitumor Activities of IKP-104 a 4-1H Pyridizinone Derivative on Cultured and Implanted Tumors", Jpn J Cancer Res, 81(12): abstract only, 1990.

Montefiori et al. "In Vitro Evaluation of Mismatched Double-Stranded RNA (Ampligen) for Combination Therapy in the Treatment of Acquired Immunodeficiency Syndrome", AIDS Res Hum Retroviruses, 5(2): abstract only, 1989.

Naranjo. "Ibogaine in psychotherapy: psychoanalysis according to Naranjo", part IV, pp. 1-2. http://www.nettuno.it/fiera/electric.italy/bwitif:html, 1969.

Nishiyama et al. "Expression of the Multidrug Transporter, P-Glycoproteiin, in Renal and Transitional Cell Carcinomas", Cancer, 71(11):3611-3619, 1993.

Nooter et al. "Multidrug Resistance (MDR) Genes in Haematological Malignancies", Cytotechnology, 12(1-3): abstract only, 1993.

Nunn-Thompson et al. "Pharmacotherapy for Making Cessation", Clin Pharm, 8(10): abstract only, 1989.

Obach et al., "Cythochrome P4502D6 Catalyzes the O-Demethylation of the Psychoactive Alkaloid Ibogaine to 12-Hydroxyibogamine" Drug Metabolism and Disposition 26(8):764-768, 1998.

O'Hearn et al. "Degenration of Prukinje Cells in Parasagittal Zones of the Cerebellar Vermis After Treatment with Ibogaine of Harmaline", Neuroscience, 55(2): abstract only, 1993.

O'Hearn et al. "Ibogaine Induces Glial Activation in Parasagittal Zones of the Cerebellum", Neuroreport, 4/3: abstract only, 1993.

Pablo et al, "Noribogaine Stimulates Naloxone-Sensitive[35S]GTPgammaS Binding," NeuroReport, 9, pp. 109-114. (Website Publication Date of Dec. 20, 1997.), 1998.

Pacifici et al. "Immunological Effect of Cocaine and Host Resistance in Mice", Int J Immunother, 8(2): abstract only, 1992.

Palyi. "Survival Responses to New Cytostatic Hexitols of P388 Mouse and K562 Leukemia Cells in Vitro", Cancer Treat. Rep., 70(2): abstract only, 1986.

Pantazis et al. "Efficacy of Camptothecin Congeners in the Treatment of Human Breast Carcinoma Xenografts", Oncology Research, 5(8): abstract only, 1994.

Pehek. "Effects of Cathinone and Amphetamine on the Neurochemistry of Dopamine in Vivo", Neuropharmacology, 29/12: abstract only, 1990.

Perera et al. "Tertiary Indole Alkaloids of *Tabernaemontana dichotoma* Seeds", Planta Med., 49/1: abstract only, 1983.

Perrin. "Clinical Pharmacokinetics of Ergotamine in Migraine and Cluster Headache", Clin. Pharmacokin., 10/4: abstract only, 1985.

Popik et al. "NMDA Antagonist Properties of the pUtative Antiaddictive Drug, Ibogaine", Journal of Pharmaceutical and Experimental Therapeutics, 275(2), 753-760, 1995.

Popik et al. "The Putative Anti-Addictive Drug Ibogaine is a Competitive Inhibitor of ( SUP 3 H) Binding to the NMDA Receptor Complex", Psychopharmacologia, 114(4): abstract only, 1994.

Popik et al. "100 Years of Ibogaine: Neurochemical and Pharmacological Actions of a Putative anti-addictive Drug", Pharmacological Reviews 47(2), pp. 235-253, 1995.

Pulvirenti et al. "Lisuride Reduces Intravenous Cocaine Self-Administration in Rats", Pharmacology, Biochemistry and Behavior, 47(4): abstract only, 1994.

Qiu et al. "The Influence of Chronic Nicotine Treatment on Stress-Induces Gastric Ulceration and Emptying Rate in Rats", Experientia, 48(4): abstract only, 1992.

Rezvani et al. "Noribogaine, a Primary Ibogaine Metabolite, Reduces Alcohol Intake in P and Fawn-Hooded Rats." RSA Annual Scientific Meeting Abstract only, 1995.

Rezvani et al. "Reduction of Alcohol Intake in Alcohol Preferring Fawn-hooded and P Rats by Noribogaine, the Primary Metabolite of Ibogaine." NIDA Monograph Series (1996) 162:281 Abstract only.

Ricceri et al. "Postnatal cocaine Esposure Affects Neonatal Passive Avoidance Performance and Cholinergic Development in Rats", Pharmacology, Biochemistry and Behavior, 45(2): abstract only, 1993.

Rodriguez et al. "Cocaine Adminstration Prior to Reactivation Facilitates Later Acquisition of an Avoidance Response in Rats", Psychopharmacologia, 112(2-3): abstract only, 1993.

Rosenmund et al. "Ibogamin, Ibogain and Epiibogamin" Chem. Ber. vol. 108, p. 1871-1895, 1975.

Sachs et al. "Corneal Complications Associated with the Use of Crack Cocaine", Ophthalmology, 100(2): abstract only, 1993.

Salmoiraghi et al. "Effects of LSD 25, BOL 148, Bufotenine, Mescaline and Ibogaine on the Potentiation of Hexobarbital Hypnosis Produced by Serotonin and Reserpine." J. Pharm and Exp Ther. vol. 120. No. 1, pp. 20-25, 1957.

Samadi-Baboli et al. "Preparation of Low Density Lipoprotein-9-Methoxy-Illipticin Complex and its Cytotoxic Effect Against L1210 and P 388 Leukemic Cells in Vitro", Eur J Cancer Clin Oncol, 25(2): abstract only, 1989.

Saper et al. "Ergotamine Tartrate Dependency: Features and Possible Mechanisms", Clin. Neuropharmacol., 9/3: abstract only, 1986.

Schecter et al. "Comparison of the Behavioral Effects of Ibogaine from Three Sources: Mediation of Discriminative Activity", European Jornal of Pharmacology, 249(1): abstract only, 1993.

Schneider et al. "Analysis of the Cardiovascular Action of Ibogaine Hydrochloride (1)" Arch. Int. Pharmacodyn. vol. 110, pp. 92-102, 1957.

Schneider et al., "Neuropharmacological Studies of Ibogaine: An Indole Alkaloid with Central Stimulant Properties" Ann. of N.Y. Acad. Sci. vol. 66, pp. 765-76, 1957.

Schneider et al., "Potentiation Action of Ibogaine on Morphine Analgesia" Experiential vol. 12, pp. 323-324, 1956.

Schnider et al. "Use and Abuse of Analgesics in Tension-Type Headache", Cephalalgia, 14/2: abstract only, 1994.

Schuckit et al. "Opioid Drug Use." in Isselbacher et al. Harrison's Principles of Internal Medicine :2425-2429, 1994.

Schuckit. "Alcohol and Alcoholism." in Isselbacher et al. Harrison's Principles of Internal Medicine :2420-2425, 1994.

Seeber et al. "In Vivo Resistance Towards Anthracyclines, Etoposide, and Cis-Diamminedichloroplatinum (II)", Cancer Res., 42(11): abstract only, 1982.

Sehested et al. "The Carboxylic Ionophore Monensin Inhibits Active Drug Efflux and Modulates in-Vitro Resistance in Daunorubicin Resistant Enrlich Ascites Tumor Cells", Biochem Pharmacol, 37(17): abstract only, 1988.

Sershen et al. "Ibogaine Antagonizes Cocaine-Induced Locomotor Stimulation in Mice", Life Sci., 50(15): abstract only, 1992.

Sershen et al. "Ibogaine Reduces Amphetamine-Induced Locomotor Stimulation in C57BL/6By Mice, but Stimulates Locomotor Activity in Rats", Life Sci., 51(13): abstract only, 1992.

Sershen et al. "Ibogaine Reduces Preference for Cocaine Consumption in C57BL/6By Mice", Pharmacol., Biochem. Behav., 47(1): abstract only, 1994.

Shen et al. "Antagonists at Excitatory Opioid Receptors on Sensory Neurons in Culture Increase Potency and Specificity of Opiate Analgesics and Attenuate Development of Tolerance / Dependence", Brain Research, 636(2): abstract only, 1994.

Sheppard. "A Preliminary Investigation of Ibogaine: Case Reports and Recommendations for Further Study", J. Subst. Abuse Treat., 11/4: abstract only, 1994.

Shir et al., "Neuropathic pain unrelieved by morphine, alleviated by haloperidol" Harefuah 118(8):452-454, Abstract only, 1990.

Shook et al. "A cyclic Somatostatin Analog that Precipitates Withdrawal in Morphine-Dependent Mice", NIDA Res. Monogr., 76(Probl. Drug Depend.): abstract only, 1987.

Sinkula et al. "Rationale for Design for Biologically Reversible Drug Derivatives: Prodrugs." Journal of Pharmaceutical Sciences, 64(2):181-210, 1975.

Slotkin et al. "A Model of Harmine Metabolism in the Rat." The Journal of Pharmacology and Experimental Therapeutics, 174(3):456-462, 1970.

Slotkin et al. "Blood Levels and Urinary Excretion of Harmine and its Metabolites in Man and Rats." The Journal of Pharmacology and Experimental Therapeutics, 173(1):26-30, 1970.

Slotkin et al. "Urinary Metabolites of Harmine in the Rat and their Inhibition of Monoamine Oxidase." Biochemical Pharmacology 19:125-131, 1970.

Sloviter et al. "A Common Mechanism of Lysergic Acid, Indolealkylamine and Phenethylamine Hallucinogens: Serotonergic Mediation of Behavioral Effects in Rats" J. Pharm. Exp. Ther. vol. 214, No. 2, pp. 231-238, 1980.

Smith. "Interaction of Biogenic Amines with Ethanol", Adv Exp Med Biol, 56: abstract only, 1975.

Solinas et al. "Solid-supported reagents and catch-and-release techniques in organic synthesis". Synthesis 20070816 DE LNKD-DOI:10.1055/S-2007-983806, No. 16., pp. 2409-2453, 2007.

Stella. "Pro-drugs: An Overview and Definition." Prodrugs as Novel Drug Delivery System. ACS Symposium Series :1-115, 1975.

Stella. "Pro-drugs as Novel Drug Delivery Systems", Higuchi, T. et al., ed. (American Chemical Society, Washington), pp. 1-49, 1975.

Sugiyama et al. "Quantitative Analysis of Cell-Kill Effects of Anticancer Drugs: Consideration of Both In Vitro and In Vivo Expreimental Systems", Gan to Kagaku Ryoho, 14(12): abstract only, 1987.

Tarnower et al. "Ergotism Masquerading as Arteritis", Postgrad Med, 85(1): abstract only, 1989.

Teoh et al. "Buprenorphine Effects on Morphine- and Cocaine-Induced Subjective Responses by Drug—Dependent Men", Journal of Clinical Psychopharmacology, 14(1): abstract only, 1994.

Tfelt-Hansen et al. "Nitroglycerin for Ergotism. Experimental Studies in Vitro and in Migraine Patients and Treatment of an Overt Case", Eur. J. Clin. Pharmacol., 22/2: abstract only, 1982.

Torrenegra et al. "Alkaloids of *Stemmadenia grandiflora*", Phytochemistry, 27(6): pp. 1843-1848, 1988.

Tsuruo. "Multidrug Resistance: A Transport System of Antitumor Agents and Xenobiotics", Princess Takamatsu Symp, 21: abstract only, 1990.

Uldry et al. "Cerebrovascular Accidents in Relation to Drug Consumption or Drug Abuse", Schweiz Rundsch Med Prax, 78(23): abstract only, 1989.

Valadez et al. "Persistence of the Ability of Amphetamine Preexposure to Facilitate Acquistion of Cocaine Self-Administration", Pharmacology, Biochemistry and Behavior, 47(1): abstract only, 1994.

Valencia et al. "Obovatine, a new bisindole alkaloid from *Stemmadenia obovata*", Journal of Natural Products, 58(1):pp. 134-137, 1995.

Vescovi et al. "Successful Treatment of Opiate Withdrawal Using Lysine Acetylsalicylate", Curr. Ther. Res., Clin. Exp., 33/5: abstract only, 1983.

Villalba et al. "Uses and Abuses of Ipecacuana Syrup", Farm. Clin., 9/1: abstract only, 1992.

Wells et al. "Recognition and Treatment of Arterial Insufficiency from Cafergot", J. Vasc. Surg., 4/1: abstract only, 1986.

Whitaker et al. "High Affinity 3H-Serotonin Binding to Caudate: Inhibition by Hallucinogenic and Serotonergic Drugs", Psychopharmacology, vol. 59, pp. 1-5, 1978.

Whitaker et al., "Selective Labeling of Serotonin Receptors by d'(3H)Lysergic Acid Diethylamide in Calf Caudate", Proc. Natl. Acad. Sci., USA vol. 75, No. 12, pp. 5783-5787, 1978.

Whittaker et al. "Recurrent Laryngeal Nerve Paralysis in Patients Receiving Vincristine and Vinblastine", Br Med J, 1(6071): abstract only, 1977.

Widler et al. "Pharmacodynamics and Pharmacokinetics of Khat: a Controlled Study", Clin. Pharmacol. Ther., 55/5: abstract only, 1994.

Wildmann. "Heterocycles as Physiological Ligands for the Benzodiazepine Receptor and for Other Binding Sites", Pharmacol Res, 21(6): abstract only, 1989.

Williams, Jr. et al. "The 'Alice in Wonderland' Experience Ergot Alkaloid Therapy for Prolactin-Secreting Pituitary Tumors", West. J. Med., 138/3: abstract only, 1983.

Wishart et al. "Is Multidrug Resistance Relevant in Breast Cancer", Eur. J. Surg. Oncol., 17/5: abstract only, 1991.

Witt et al. "Pharmacodynamic and Pharmacokinetic Characterization of Poly(Ethylene glycol) Conjugation to Met-Enkephalin Analog [$_D$-Pen$^2$, $_D$-Pen$^5$]-enkephalin (DPDPE)", J. of Pharm. and Exp. Thera., 298(2), pp. 848-856, 2001.

Witt et al. "Pluronic P85 Block Copolymer Enhances Opioid Pepetide Analgesia", J. of Pharm. and Exp. Thera., 303(2), pp. 760-767, 2002.

Worz. "Effects and Risks of Psychotropic and Analgesic Combinations", Am. J. Med., 75/5A: abstract.

Zetler et al. "Pharmacokinetics in the Rat of the Hallucinogenic Alkaloids Harmine and Harmaline." Naunyn-Schmiedeberg's Arch. Pharmacol., 285, 273-292, 1974.

Zetler et al. "Cerebral Pharmacokinetics of Tremor-Producing Harmala and Iboga Alkaloids"Pharmacology vol. 7, No. 4, pp. 237-248, 1972.

* cited by examiner

SUBSTITUTED NORIBOGAINE

CROSS-REFERENCE TO RELATED APPLICATIONS

This application claims priority under 35 U.S.C. §119(e) to U.S. Provisional Patent Application Ser. No. 61/333,668, filed on May 11, 2010, and to U.S. Provisional Patent Application Ser. No. 61/419,776, filed on Dec. 3, 2010, both of which applications are incorporated by reference herein in their entirety.

FIELD OF THE INVENTION

This invention relates noribogaine derivatives, compositions and methods of use thereof.

STATE OF THE ART

Noribogaine is a well known derivative of ibogaine and is sometimes referred to as 12-hydroxyibogaine. It is a metabolite of ibogaine. U.S. Pat. No. 2,813,873 claims noribogaine albeit as "12-O-demethylibogaine" while providing an incorrect structural formula for ibogaine. The structure of noribogaine has now been thoroughly evaluated and is found to combine the features of tryptamine, tetrahydrohavaine and indolazepines. Noribogaine can be depicted by the following formula:

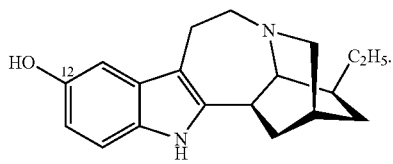

Noribogaine and its pharmaceutically acceptable salts have recently received significant attention as a non-addictive alkaloid useful in treating addiction (U.S. Pat. No. 6,348,456) and as a potent analgesic (U.S. Pat. No. 7,220,737).

Noribogaine has been found to have properties suitable for the treatment of pain and to the withdrawal symptoms associated with drug dependency or abuse. In particular, it is believed that noribogaine binds to two classes of opioid receptors that have been associated with pain relief, the μ and κ receptors. In the case of the μ-type receptors, it appears that noribogaine acts as an opiate agonist. In addition, noribogaine elevates brain serotonin levels by blocking synaptic reuptake. It is believed that such levels (as well as ligand interactions at the μ and κ opiate receptors) play a role in the anxiety and drug cravings experienced by addicts during withdrawal.

SUMMARY OF THE INVENTION

This invention relates to noribogaine derivative compounds. Such compounds are contemplated as being useful in treating drug addiction and/or pain. Accordingly, in one of its compound aspects, this invention is directed to a compound or a pharmaceutically acceptable salt thereof wherein said compound is represented by Formula I:

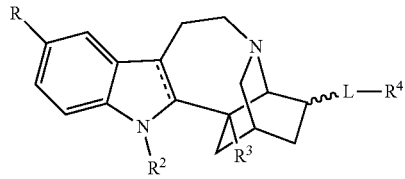

wherein

------ is a single or double bond;

R is halo, $OR^1$, or $C_1$-$C_{12}$ alkyl optionally substituted with 1 to 5 $R^9$;

$R^1$ is hydrogen or a hydrolysable group selected from the group consisting of —C(O)X, —C(O)OX and —C(O)N(Y)$_2$ where each X is selected from the group consisting of $C_1$-$C_6$ alkyl optionally substituted with 1 to 5 $R^9$, and each Y is independently selected from the group consisting of hydrogen, $C_1$-$C_6$ alkyl optionally substituted with 1 to 5 $R^9$, $C_6$-$C_{14}$ aryl optionally substituted with 1 to 5 $R^9$, $C_3$-$C_{10}$ cycloalkyl optionally substituted with 1 to 5 $R^9$, $C_1$-$C_{10}$ heteroaryl having 1 to 4 heteroatoms and which is optionally substituted with 1 to 5 $R^9$, $C_1$-$C_{10}$ heterocyclic having 1 to 4 heteroatoms and which is optionally substituted with 1 to 5 $R^9$, and where each Y, together with the nitrogen atom bound thereto form a $C_1$-$C_6$ heterocyclic having 1 to 4 heteroatoms and which is optionally substituted with 1 to 5 $R^9$ or a $C_1$-$C_6$ heteroaryl having 1 to 4 heteroatoms and which is optionally substituted with 1 to 5 $R^9$;

$R^2$ is selected from the group consisting of hydrogen, $C_1$-$C_{12}$ alkyl optionally substituted with 1 to 5 $R^9$, aryl optionally substituted with 1 to 5 $R^9$, —C(O)$R^5$, —C(O)NR$^5$R$^5$ and —C(O)OR$^5$;

$R^3$ is selected from the group consisting of hydrogen, —(CH$_2$)$_m$OR$^7$, —CR$^6$(OH)R$^7$, —(CH$_2$)$_m$CN, —(CH$_2$)$_m$ OR$^7$, —(CH$_2$)$_m$CO$_2$R$^7$, —(CH$_2$)$_m$C(O)NR$^6$R$^7$, —(CH$_2$)$_m$C(O)NR$^6$NR$^7$R$^7$, —(CH$_2$)$_m$C(O)NR$^6$NR$^7$C(O)R$^8$, and —(CH$_2$)$_m$NR$^6$R$^7$;

m is 0, 1, or 2;

L is a bond or $C_1$-$C_{12}$ alkylene;

$R^4$ is selected from the group consisting of hydrogen, $C_1$-$C_{12}$ alkyl substituted with 1 to 5 $R^9$, $C_2$-$C_{12}$ alkenyl substituted with 1 to 5 $R^9$, —X$^2$—R$^6$, —(X$^2$—Y$^2$)$_n$—X$^2$—R$^6$, —SO$_2$NR$^6$R$^7$, —O—C(O)R$^8$, —C(O)OR$^7$, —C(O)NR$^6$R$^7$, —NR$^6$R$^7$, —NHC(O)R$^8$, and —NR$^6$C(O)R$^8$;

each $R^5$ is independently selected from the group consisting of hydrogen, $C_1$-$C_{12}$ alkyl, $C_2$-$C_{12}$ alkenyl, $C_2$-$C_{12}$ alkynyl, $C_6$-$C_{10}$ aryl, $C_1$-$C_6$ heteroaryl having 1 to 4 heteroatoms, and $C_1$-$C_6$ heterocycle having 1 to 4 heteroatoms, and wherein the alkyl, alkenyl, alkynyl, aryl, heteroaryl, and heterocycle are optionally substituted with 1 to 5 $R^9$;

$X^2$ is selected from the group consisting of O and S;

$Y^2$ is $C_1$-$C_4$ alkylene or $C_6$-$C_{10}$ arylene, or a combination thereof;

n is 1, 2, or 3;

$R^6$ and $R^7$ are each independently selected from the group consisting of hydrogen, $C_1$-$C_{12}$ alkyl optionally substituted with 1 to 5 $R^9$, $C_1$-$C_6$ heterocycle having 1 to 4 heteroatoms and which is optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$;

$R^8$ is selected from the group consisting of $C_1$-$C_{12}$ alkyl optionally substituted with 1 to 5 $R^9$, $C_1$-$C_6$ heterocycle having 1 to 4 heteroatoms optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$;

$R^9$ is selected from the group consisting of $C_1$-$C_4$ alkyl, phenyl, halo, —$OR^{10}$, —CN, —$COR^{10}$, —$CO_2R^{10}$, —C(O)$NHR^{10}$, —$NR^{10}R^{10}$, —C(O)$NR^{10}R^{10}$, —C(O)$NHNHR^{10}$, —C(O)$NR^{10}NHR^{10}$, —C(O)$NR^{10}NR^{10}R^{10}$, —C(O)$NHNR^{10}C(O)R^{10}$, —C(O)$NHNHC(O)R^{10}$, —$SO_2NR^{10}R^{10}$, —C(O)$NR^{10}NR^{10}C(O)R^{10}$, and —C(O)$NR^{10}NHC(O)R^{10}$; and $R^{10}$ is independently hydrogen or $C_1$-$C_{12}$ alkyl;

provided that:

when L is a bond, then $R^4$ is not hydrogen;

when ====== is a double bond, R is an ester hydrolyzable group, $R^2$ and $R^3$ are both hydrogen, then -L-$R^4$ is not ethyl;

when ====== is a double bond, R is —OH, halo or $C_1$-$C_{12}$ alkyl optionally substituted with 1 to 5 $R^9$, then $R^3$ is hydrogen; and when ====== is a double bond, R is $OR^1$, $R^3$ is hydrogen, -L-$R^4$ is ethyl, then $R^1$ is not a hydrolyzable group selected from the group consisting of an ester, amide, carbonate and carbamate.

This invention is also directed to pharmaceutical compositions comprising a pharmaceutically acceptable excipient and a therapeutically effective amount of a compound of this invention or a mixture of one or more of such compounds.

This invention is still further directed to methods for treating pain and/or addiction in a patient in need thereof, which methods comprise administering to the patient a one or more of compounds or a pharmaceutical composition of this invention.

DETAILED DESCRIPTION OF THE INVENTION

This invention is directed to ribose substituted noribogaine for use in treating pain and/or addition. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically acceptable excipient" includes a plurality of pharmaceutically acceptable excipients.

1. DEFINITIONS

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

Noribogaine can be depicted by the following Formula:

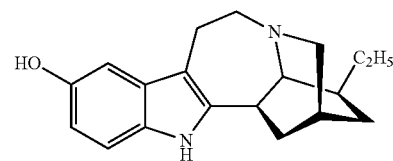

and can be synthesized by the O-demethylation of ibogaine. This may be accomplished, for example, by reacting ibogaine with boron tribromide/methylene chloride at room temperature and then purifying the product using known procedures. Ibogaine may be obtained from natural or commercial sources, or can be synthesized by methods known in the art (see Huffman, et al., J. Org. Chem. 50:1460 (1985)). In addition, noribogaine may also be obtained from the National Institute on Drug Abuse (Rockville, Md.).

As used herein, the term "hydrolyzable group" refers to a group that can be hydrolyzed to release the free hydroxy group under hydrolysis conditions. Examples of hydrolysable group include, but are not limited to those defined for $R^1$ above. Preferred hydrolysable groups include carboxyl esters, phosphates and phosphate esters. The hydrolysis may be done by chemical reactions conditions such as base hydrolysis or acid hydrolysis or may be done in vivo by biological processes, such as those catalyzed by a phosphate hydrolysis enzyme. Nonlimiting examples of hydrolysable group include groups linked with an ester-based linker (—C(O)O— or —OC(O)—), an amide-based linker (—C(O)$NR^{40}$— or —$NR^{40}$C(O)—), or a phosphate-linker (—P(O)($OR^{40}$)—O—, —O—P(S)($OR^{40}$)—O—, —O—P(S)($SR^{40}$)—O—, —S—P(O)($OR^{40}$)—O—, —O—P(O)($OR^{40}$)—S—, —S—P(O)($OR^{40}$)—S—, —O—P(S)($OR^{40}$)—S—, —S—P(S)($OR^{40}$)—O—, —O—P(O)($R^{40}$)—O—, —O—P(S)($R^{40}$)—O—, —S—P(O)($R^{40}$)—O—, —S—P(S)($R^{40}$)—O—, —S—P(O)($R^{40}$)—S—, or —O—P(S)($R^{40}$)—S—) where $R^{40}$ can be hydrogen or alkyl.

"Alkyl" refers to alkyl groups having from 1 to 12 carbon atoms, preferably 1 to 6 carbon atoms and more preferably 1 to 3 carbon atoms. The alkyl group may contain linear or branched carbon chains. This term is exemplified by groups such as methyl, ethyl, n-propyl, iso-propyl, n-butyl, t-butyl, n-pentyl and the like. The term "$C_x$ alkyl" refers to an alkyl group having x carbon atoms, wherein x is an integer, for example, $C_3$ refers to an alkyl group having 3 carbon atoms.

"Alkenyl" refers to straight or branched hydrocarbyl groups having from 2 to 12 carbon atoms, preferably 2 to 6 carbon atoms and more preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 12 carbon atoms, preferably 2 to 6 carbon atoms and more preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH).

"Alkoxy" refers to the group —O-alkyl wherein alkyl is as defined herein. Alkoxy includes, by way of example, methoxy, ethoxy, n-propoxy, iso-propoxy, n-butoxy, t-butoxy, sec-butoxy, n-pentoxy and the like.

"Acyl" refers to the groups $R^{41}$—C(O)—, wherein $R^{41}$ is selected from the group consisting of hydrogen, alkyl, cycloalkyl, aryl, heteroaryl, and heterocyclic, wherein alkyl, cycloalkyl, aryl, heteroaryl, and heterocyclic are as defined herein and are optionally substituted with 1 to 5 substituents independently selected from the group consisting of halo, $C_1$ to $C_3$ alkyl, hydroxyl, and $C_1$ to $C_3$ alkoxy.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom.

"Aryloxy" refers to the group —O-aryl wherein aryl is as defined herein. Aryloxy includes, by way of example, methoxy, ethoxy, n-propoxy, iso-propoxy, n-butoxy, t-butoxy, sec-butoxy, n-pentoxy and the like.

"Carboxyl" refers to —COOH or salts thereof.

"Carboxyl esters" refers to the groups —C(O)O—$R^{42}$, wherein $R^{42}$ is selected from the group consisting of hydrogen, alkyl, cycloalkyl, aryl, heteroaryl, and heterocyclic, wherein alkyl, cycloalkyl, aryl, heteroaryl, and heterocyclic are as defined herein and are optionally substituted with 1 to 5 substituents independently selected from the group consisting of halo, $C_1$ to $C_3$ alkyl, hydroxyl, and $C_1$ to $C_3$ alkoxy.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Halo" or "halogen" refers to fluoro, chloro, bromo and iodo and preferably is fluoro or chloro.

"Heteroaryl" refers to an aromatic group of from 1 to 10 carbon atoms and 1 to 4 heteroatoms selected from the group consisting of oxygen, nitrogen, sulfur within the ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Examples of heteroaryls include pyridyl, pyrrolyl, indolyl, thiophenyl, and furyl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Alkylene" refers to a divalent radical of an alkyl group. "Methylene" refers to the group —CH$_2$—.

"Arylene" refers to a divalent radical of an aryl group. "Phenylene" refers to the divalent phenyl group —C$_6$H$_4$—.

It is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

The term "pharmaceutically acceptable prodrugs" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

"Pharmaceutically acceptable salt" refers to pharmaceutically acceptable salts, including partial salts, of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, lactate, succinate, citrate, salicylate, malate, maleate, oxalate, phosphate, phosphite, sulfate, nitrate, perchlorate, aconitate, thalate, embonate, enanthate, and the like.

"Pharmaceutically acceptable partial salts" refers to compounds having a substituent capable of having more than one group form a salt but less than the maximum amount of such groups actually form a salt. For example, a diphospho group can form a plurality of salts and, if only partially ionized, the resulting group is sometimes referred to herein as a partial salt.

As used herein, the term "therapeutically effective amount" refers to the amount of a composition of this invention that is sufficient to effect treatment, as defined herein, when administered to a subject in need of such treatment. The therapeutically effective amount will vary depending upon the subject and condition being treated, the weight and age of the subject, the severity of the condition, the particular composition or excipient chosen, the dosing regimen to be followed, timing of administration, the manner of administration and the like, all of which can be determined readily by one of ordinary skill in the art.

As used herein, the term "treatment" or "treating" means any treatment of a disease or condition in a patient, including:
  preventing or protecting against the disease or condition, that is, causing the clinical symptoms not to develop, for example, in a subject at risk of suffering from such a disease or condition, thereby substantially averting onset of the disease or condition;
  inhibiting the disease or condition, that is, arresting or suppressing the development of clinical symptoms; and/or
  relieving the disease or condition that is, causing the regression of clinical symptoms.

As used herein, the term "pain" refers to all types of pain, including neuropathic and nociceptive pain. It is also contemplated that the compositions disclosed herein can be used to treat other types of pain such as phantom pain which is the sensation of pain from a limb or organ that has been lost or from which a person no longer receives physical signals, and is an experience almost universally reported by amputees and quadriplegics.

As used herein, the term "addiction" refers to a persistent behavioral pattern marked by physical and/or psychological dependency to a substance, particularly drugs such as narcotics, stimulants, and sedatives, including but not limited to heroin, cocaine, alcohol, nicotine, caffeine, amphetamine, desoxyephedrine, methadone and combinations thereof. As used herein, the "treatment of addiction in a patient" refers to reducing the withdrawal symptoms associated with drug dependency as well as alleviating drug cravings in addicts. Such symptoms include nausea, vomiting, anxiety, abdominal cramps, muscle pain, chills and headache.

As used herein, the term "patient" refers to mammals and includes humans and non-human mammals.

2. COMPOUNDS

This invention is relates to noribogaine derivative compounds. Such compounds are contemplated as being useful in treating pain and/or drug dependency. Accordingly, in one of its composition aspects, this invention is directed to a compound or a pharmaceutically acceptable salt thereof wherein said compound is represented by Formula I:

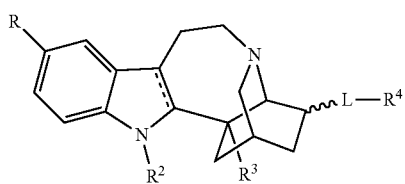

I wherein
  ------ is a single or double bond;
  R is halo, $OR^1$, or $C_1$-$C_{12}$ alkyl optionally substituted with 1 to 5 $R^9$;
  $R^1$ is hydrogen or a hydrolysable group selected from the group consisting of —C(O)X, —C(O)OX and —C(O)N(Y)$_2$ where each X is selected from the group consisting of $C_1$-$C_6$ alkyl optionally substituted with 1 to 5 $R^9$, and each Y is independently selected from the group consisting of hydrogen, $C_1$-$C_6$ alkyl optionally substituted with 1 to 5 $R^9$, $C_6$-$C_{14}$ aryl optionally substituted with 1 to 5 $R^9$, $C_3$-$C_{10}$ cycloalkyl optionally substituted with 1 to 5 $R^9$, $C_1$-$C_{10}$ heteroaryl having 1 to 4 heteroatoms and which is optionally substituted with 1 to 5 $R^9$, $C_1$-$C_{10}$ heterocyclic having 1 to 4 heteroatoms and which is optionally substituted with 1 to 5 $R^9$, and where each Y, together with the nitrogen atom bound thereto form a $C_1$-$C_6$ heterocyclic having 1 to 4 heteroatoms and which is optionally substituted with 1 to 5 $R^9$ or a $C_1$-$C_6$ heteroaryl having 1 to 4 heteroatoms and which is optionally substituted with 1 to 5 $R^9$;
  $R^2$ is selected from the group consisting of hydrogen, $C_1$-$C_{12}$ alkyl optionally substituted with 1 to 5 $R^9$, aryl optionally substituted with 1 to 5 $R^9$, —C(O)$R^5$, —C(O)NR$^5$R$^5$ and —C(O)OR$^5$;
  $R^3$ is selected from the group consisting of hydrogen, —(CH$_2$)$_m$OR$^7$, —CR$^6$(OH)R$^7$, —(CH$_2$)$_m$CN, —(CH$_2$)$_m$ COR$^7$, —(CH$_2$)$_m$CO$_2$R$^7$, —(CH$_2$)$_m$C(O)NR$^6$R$^7$, —(CH$_2$)$_m$C(O)NR$^6$NR$^7$R$^7$, —(CH$_2$)$_m$C(O)NR$^6$NR$^7$C(O)R$^8$, and —(CH$_2$)$_m$NR$^6$R$^7$;
  m is 0, 1, or 2;
  L is a bond or $C_1$-$C_{12}$ alkylene;
  $R^4$ is selected from the group consisting of hydrogen, $C_1$-$C_{12}$ alkyl substituted with 1 to 5 $R^9$, $C_2$-$C_{12}$ alkenyl substituted with 1 to 5 $R^9$, —X$^2$—R$^6$, —(X$^2$—Y$^2$)$_n$—X$^2$—R$^6$, —SO$_2$NR$^6$R$^7$, —O—C(O)R$^8$, —C(O)OR$^7$, —C(O)NR$^6$R$^7$, —NR$^6$R$^7$, —NHC(O)R$^8$, and —NR$^6$C(O)R$^8$;
  each $R^5$ is independently selected from the group consisting of hydrogen, $C_1$-$C_{12}$ alkyl, $C_2$-$C_{12}$ alkenyl, $C_2$-$C_{12}$ alkynyl, $C_6$-$C_{10}$ aryl, $C_1$-$C_6$ heteroaryl having 1 to 4 heteroatoms, and $C_1$-$C_6$ heterocycle having 1 to 4 heteroatoms, and wherein the alkyl, alkenyl, alkynyl, aryl, heteroaryl, and heterocycle are optionally substituted with 1 to 5 $R^9$;
  $X^2$ is selected from the group consisting of O and S;
  $Y^2$ is $C_1$-$C_4$ alkylene or $C_6$-$C_{10}$ arylene, or a combination thereof;
  n is 1, 2, or 3;
  $R^6$ and $R^7$ are each independently selected from the group consisting of hydrogen, $C_1$-$C_{12}$ alkyl optionally substituted with 1 to 5 $R^9$, $C_1$-$C_6$ heterocycle having 1 to 4 heteroatoms and which is optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$;
  $R^8$ is selected from the group consisting of $C_1$-$C_{12}$ alkyl optionally substituted with 1 to 5 $R^9$, $C_1$-$C_6$ heterocycle having 1 to 4 heteroatoms optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$heteroaryl having 1 to 4 heteroatoms optionally substituted with 1 to 5 $R^9$;
  $R^9$ is selected from the group consisting of $C_1$-$C_4$ alkyl, phenyl, halo, —OR$^{10}$, —CN, —COR$^{10}$, —CO$_2$R$^{10}$, —C(O)NHR$^{10}$, —NR$^{10}$R$^{10}$, —C(O)NR$^{10}$R$^{10}$, —C(O)NHNHR$^{10}$, —C(O)NR$^{10}$NHR$^{10}$, —C(O)NR$^{10}$NR$^{10}$R$^{10}$, —C(O)NHNR$^{10}$C(O)R$^{10}$, —C(O)NHNHC(O)R$^{10}$, —SO$_2$NR$^{10}$R$^{10}$, —C(O)NR$^{10}$NR$^{10}$C(O)R$^{10}$, and —C(O)NR$^{10}$NHC(O)R$^{10}$; and
  $R^{10}$ is independently hydrogen or $C_1$-$C_{12}$ alkyl;
  provided that:
  when L is a bond, then $R^4$ is not hydrogen;
  when ------ is a double bond, R is an ester hydrolyzable group, $R^2$ and $R^3$ are both hydrogen, then -L-$R^4$ is not ethyl;

when ------ is a double bond, R is —OH, halo or C$_1$-C$_{12}$ alkyl optionally substituted with 1 to 5 R$^9$, then R$^3$ is hydrogen; and when ------ is a double bond, R is OR$^1$, R$^3$ is hydrogen, -L-R$^4$ is ethyl, then R$^1$ is not a hydrolyzable group selected from the group consisting of an ester, amide, carbonate and carbamate.

In one embodiment, the compound of Formula I is represented by Formula IA:

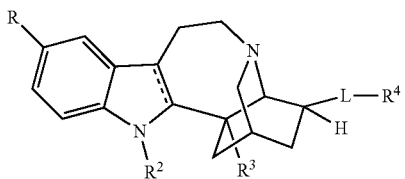

IA wherein ------ is a single or double bond and R, R$^2$, R$^3$ and R$^4$ are as described for formula I.

In one embodiment, R is halo, such as fluoro or chloro.

In one embodiment, R is C$_1$-C$_{12}$ alkyl optionally substituted with 1 to 5 R$^9$. In some embodiments, R is C$_1$-C$_{12}$ alkyl optionally substituted with a —SO$_2$NR$^6$R$^7$ group.

In another embodiment, R is OR$^1$. In some embodiments, R$^1$ is selected from the group consisting of C(O)R$^5$; —C(O)NR$^5$R$^5$ and —C(O)OR$^5$; where each R$^5$ is independently selected from the group consisting of hydrogen, alkyl, alkenyl, alkynyl, aryl, heteroaryl, and heterocycle, and wherein the alkyl, alkenyl, alkynyl, aryl, heteroaryl, and heterocycle are optionally substituted with 1 to 5 R$^9$.

In another embodiment, R$^1$ is —C(O)R$^5$, and wherein R$^5$ is C$_1$-C$_{12}$ alkyl or substituted C$_1$-C$_{12}$ alkyl or aryl, which C$_1$ to C$_{12}$ alkyl or aryl is optionally substituted with C$_1$ to C$_3$ alkyl, C$_1$ to C$_3$ alkoxy or aryl. In some embodiments, R is C$_1$-C$_6$ alkyl.

In some embodiments, R$^5$ is selected from the group consisting of methyl, ethyl, n-propyl, n-butyl, n-pentyl, n-hexyl, n-heptyl, n-octyl, n-nonyl, n-decyl, n-undecyl, n-dodecyl, iso-propyl sec-butyl, tert-butyl, phenyl, benzyl, methylbenzyl, and methoxybenzyl.

In some embodiments, R$^1$ is benzoyl.

In some embodiments, R$^1$ is hydrogen.

In some embodiments, R$^2$ is hydrogen. In some embodiments, R$^2$ is C$_1$-C$_{12}$alkyl optionally substituted with 1 to 5 R$^9$, for example, CH$_2$OH. In some embodiments, R$^2$ is aryl optionally substituted with 1 to 5 R$^9$, for example, phenyl substituted with a halo group. In some embodiments, R$^2$ is —C(O)R$^5$, such as —C(O)CH$_2$CH$_2$N(CH$_3$)$_2$. In some embodiments, R$^2$ is —C(O)NR$^5$R$^5$, such as —C(O)NHCH$_3$ or C(O)NHCH$_2$CH$_2$N(CH$_3$)$_2$. In some embodiments, R$^2$ is —C(O)OR$^5$, for example, —C(O)OCH$_3$ or —C(O)OCH$_2$CH$_2$N(CH$_3$)$_2$.

In some embodiments, R$^3$ is hydrogen or —CH$_2$OH. In some embodiments, R$^3$ is —CO$_2$R$^7$.

In some embodiments, L-R$^4$ is not ethyl. In some embodiments, L-R$^4$ is not alkyl. In some embodiments, when R is OR$^1$, L-R$^4$ is not ethyl. In some embodiments, when R is OR$^1$, L-R$^4$ is not alkyl.

In some embodiments, L is C$_1$-C$_6$alkylene.

In some embodiments, R$^4$ is X$^2$—R$^7$.

In some embodiments, X$^2$ is O.

In some embodiments, R$^4$ is selected from the group consisting of hydrogen, C$_1$-C$_{12}$alkyl, —CH$_2$Ph, and —C(O)OR$^7$.

In some embodiments, R$^4$ is —NH$_2$, —CH$_2$OCH$_2$CH$_2$OCH$_3$ or —OCH$_3$.

In some embodiments, the compound is selected from the group consisting of:

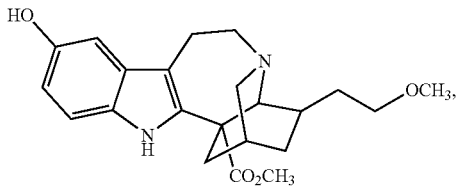

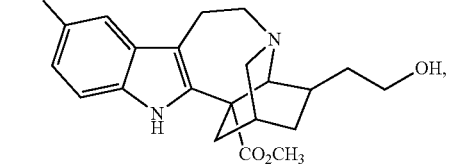

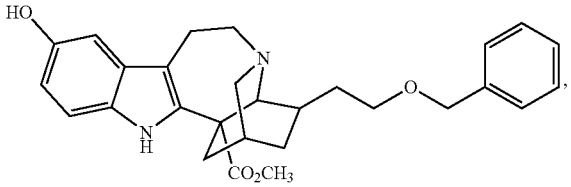

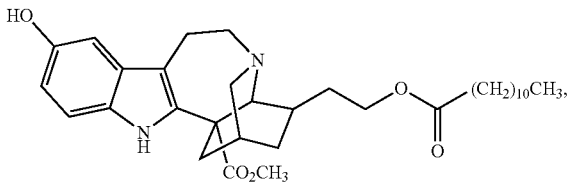

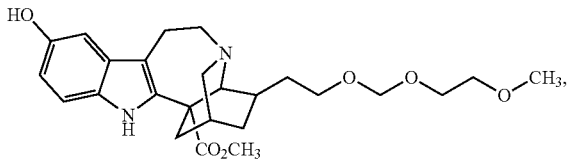

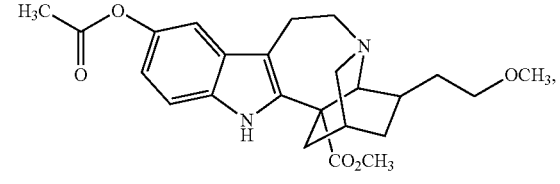

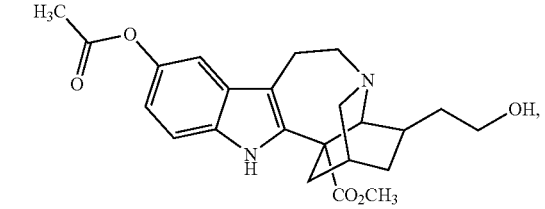

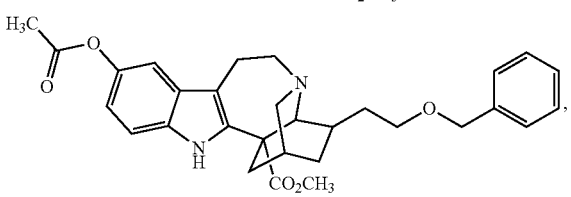

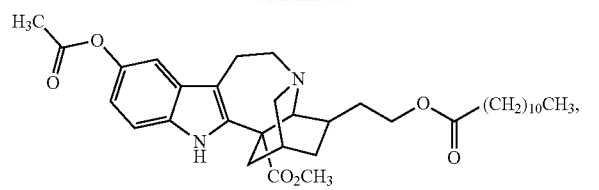
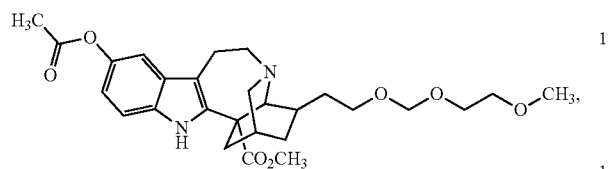
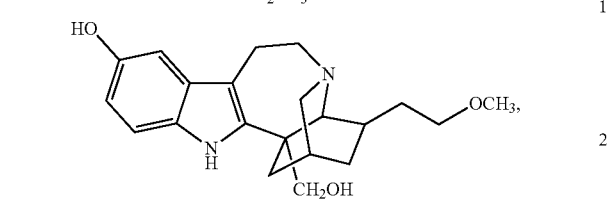
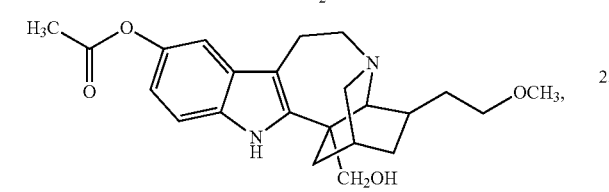
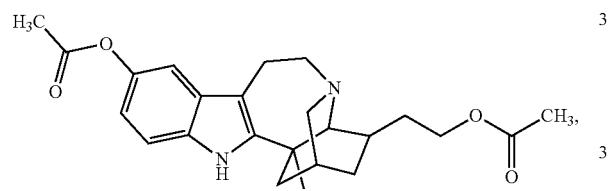
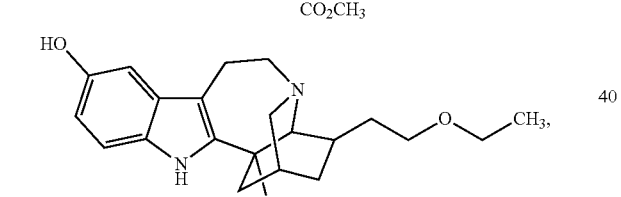
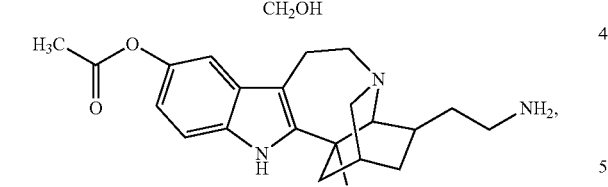
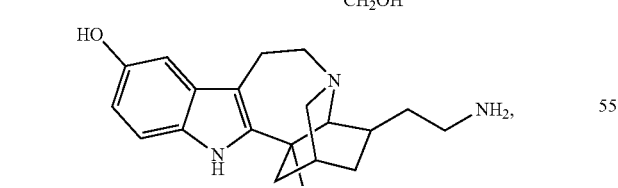
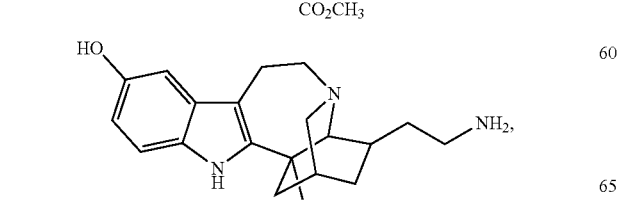
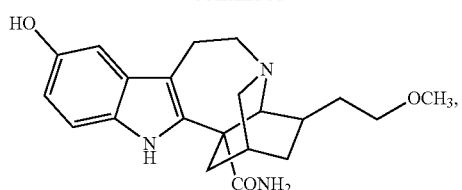
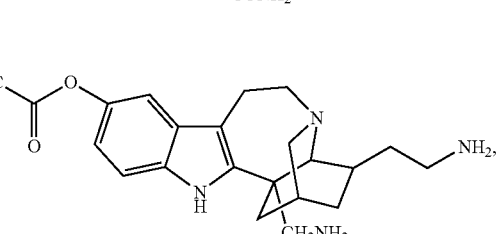
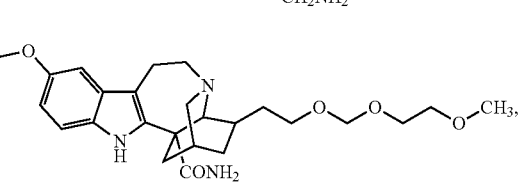
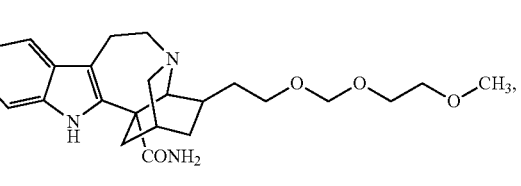
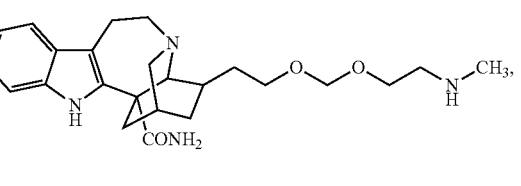
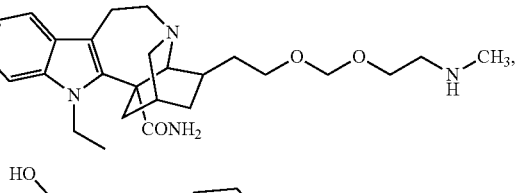
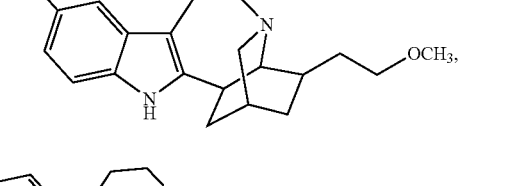
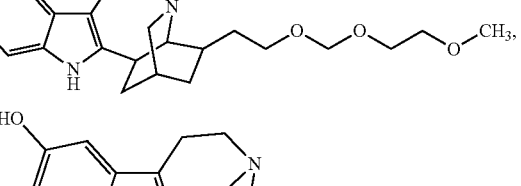
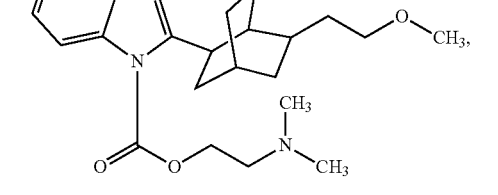

-continued

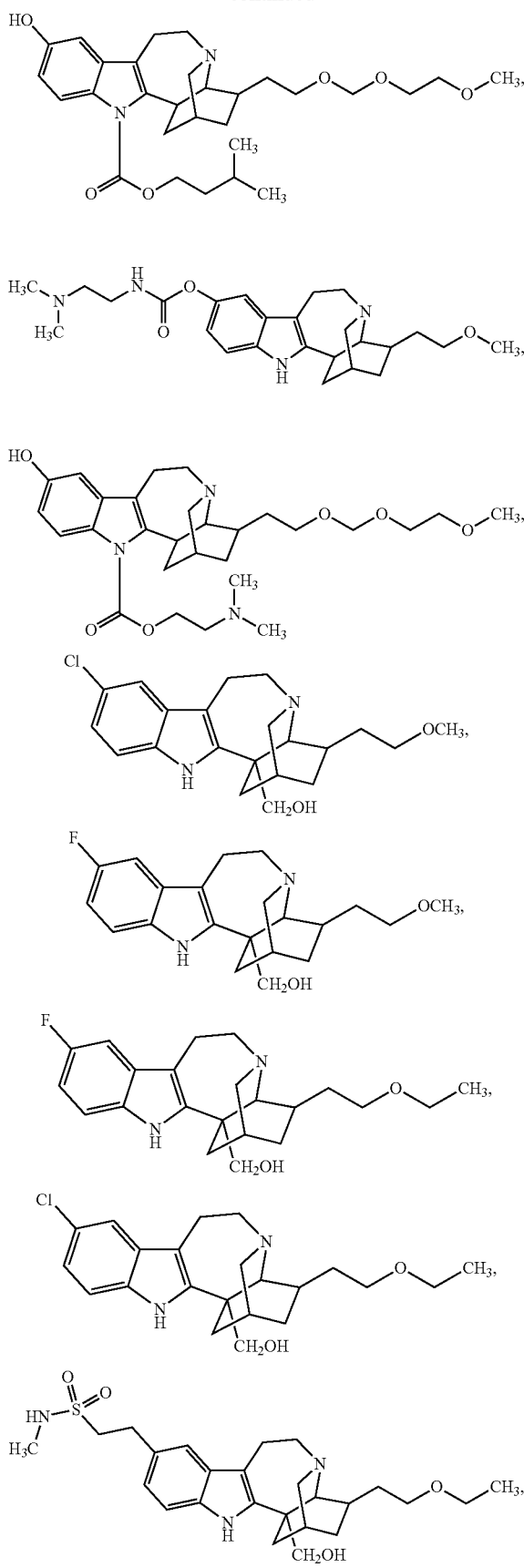

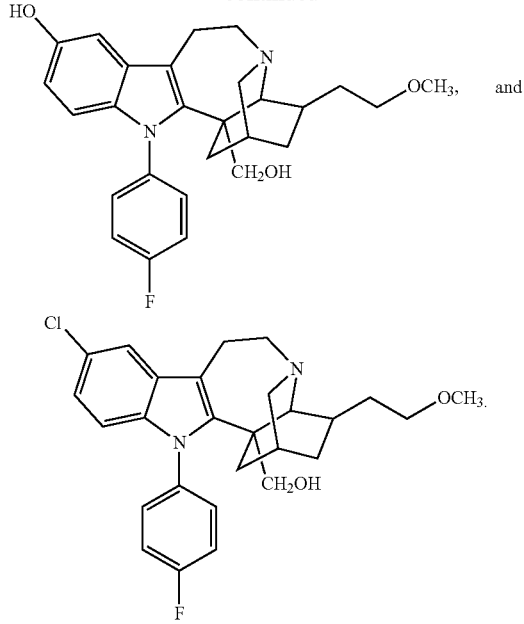

or a pharmaceutically acceptable salt thereof.

In a further embodiment, this invention is directed to a compound or a pharmaceutically acceptable salt thereof wherein said compound is represented by Formula II:

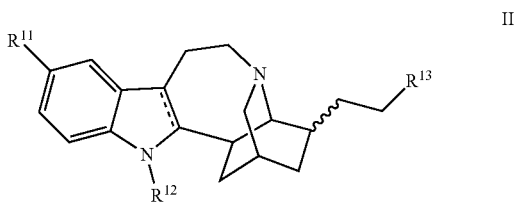

II wherein

===== is a single or double bond;

$R^{11}$ is halo, —OH, —SH, —$NH_2$, —$S(O)_2N(R^{16})_2$, —$X^1H$, —$X^1$-$L^1$-$R^{17}$, —$X^1$-$L^1$-$R^{18}$, —$X^1$-$L^1$-$R^{19}$ or —$X^1$-$L^1$-$CHR^{17}R^{18}$, where $X^1$ is O, S or $NR^{16}$;

$L^1$ is alkylene, arylene, —C(O)-alkylene, —C(O)-arylene, —C(O)O-arylene, —C(O)O-alkylene, —C(O)$NR^{19}$-alkylene, —C(O)$NR^{19}$-arylene, —C($NR^{19}$)$NR^{19}$-alkylene or —C($NR^{19}$)$NR^{19}$-arylene, wherein $L^1$ is configured such that —O-$L^1$-$R^{17}$ is —OC(O)-alkylene-$R^{17}$, —OC(O)O-arylene-$R^{17}$, —OC(O)O-alkylene-$R^{17}$, —OC(O)-arylene-$R^{17}$, —OC(O)$NR^{19}$-alkylene-$R^{17}$, —OC(O)$NR^{19}$-arylene-$R^{17}$, —OC($NR^{19}$)$NR^{19}$-alkylene-$R^{17}$ or —OC($NR^{19}$)$NR^{19}$-arylene-$R^{17}$, and wherein the alkylene and arylene are optionally substituted with 1 to 2 $R^{15}$;

$R^{12}$ is hydrogen, —$S(O)_2OR^{19}$, —$S(O)_2R^{19}$, —C(O)$R^{14}$, —C(O)$NR^{14}R^{14}$, —C(O)$OR^{14}$, $C_1$-$C_{12}$ alkyl optionally substituted with 1 to 5 $R^{15}$, $C_1$-$C_{12}$ alkenyl optionally substituted with 1 to 5 $R^{15}$, or aryl optionally substituted with 1 to 5 $R^{15}$;

$R^{13}$ is hydrogen, halo, —$OR^{16}$, —CN, $C_1$-$C_{12}$ alkyl, $C_1$-$C_{12}$ alkoxy, aryl or aryloxy, where the alkyl, alkoxy, aryl, and aryloxy are optionally substituted with 1 to 5 $R^{15}$;

each $R^{14}$ is independently selected from the group consisting of hydrogen, $C_1$-$C_{12}$ alkyl, $C_2$-$C_{12}$ alkenyl, $C_2$-$C_{12}$ alkynyl, aryl, heteroaryl, and heterocycle, and wherein the alkyl, alkenyl, alkynyl, aryl, heteroaryl, and heterocycle are optionally substituted with 1 to 5 $R^{15}$;

$R^{15}$ is selected from the group consisting of phenyl, halo, —$OR^{16}$, —CN, —$COR^{16}$, —$CO_2R^{16}$, —$NR^{16}R^{16}$, —$NR^{16}C(O)R^{16}$, —$NR^{16}SO_2R^{16}$, —$C(O)NR^{16}R^{16}$, —$C(O)NR^{16}NR^{16}R^{16}$, —$SO_2NR^{16}R^{16}$ and —$C(O)NR^{16}NR^{16}C(O)R^{16}$;

each $R^{16}$ is independently hydrogen or $C_1$-$C_{12}$ alkyl optionally substituted with from 1 to 3 halo;

$R^{17}$ is hydrogen, —$C(O)R^{19}$, —$C(O)OR^{19}$, —$C(O)N(R^{19})_2$ or —$N(R^{19})C(O)R^{19}$;

$R^{18}$ is hydrogen, —$N(R^{19})_2$, —$C(O)N(R^{19})_2$, —$C(NR^{19})N(R^{19})_2$, —$C(NSO_2R^{19})N(R^{19})_2$, —$NR^{19}C(O)N(R^{19})_2$, —$NR^{19}C(S)N(R^{19})_2$, —$NR^{19}C(NR^{19})N(R^{19})_2$, —$NR^{19}C(NSO_2R^{19})N(R^{19})_2$ or tetrazole; and each $R^{19}$ is independently selected from the group consisting of hydrogen, $C_1$-$C_{12}$ alkyl and aryl;

when ------ is a double bond and $R^{12}$ and $R^{13}$ are hydrogen, then $R^{11}$ is not hydroxy;

when ------ is a double bond, $R^{13}$ is hydrogen, $R^{11}$ is —$O$-$L^1$-$R^{17}$, —$O$-$L^1$-$R^{18}$, —$O$-$L^1$-$R^{19}$, and $L^1$ is alkylene, then —$O$-$L^1$-$R^{17}$, —$O$-$L^1$-$R^{18}$, —$O$-$L^1$-$R^{19}$ are not methoxy; and when ------ is a double bond, $R^{13}$ is hydrogen, $X^1$ is O, $L^1$ is —C(O)-alkylene, —C(O)-arylene, —C(O)O-arylene, —C(O)O-alkylene, —C(O)$NR^{19}$-alkylene, or —C(O)$NR^{19}$-arylene, then none of $R^{17}$, $R^{18}$ or $R^{19}$ are hydrogen.

In one embodiment, the compound of Formula II is represented by Formula IIA:

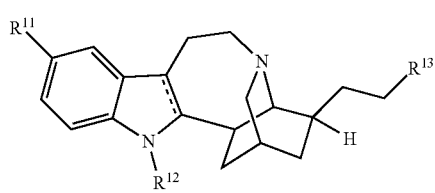

IIA wherein ------ is a double bond and each of $R^{11}$, $R^{12}$ and $R^{13}$ are as described for Formula II.

In one embodiment of the compounds of Formula II or IIA, ------ is a single bond. In another embodiment of the compounds of Formula II or IIA, ------ is a double bond.

In one embodiment of the compounds of Formula II or IIA, $R^{11}$ is halo. In certain embodiments of the compounds of Formula II or IIA, $R^{11}$ is bromo. In certain embodiments, $R^{11}$ is chloro. In certain embodiments of the compounds of Formula II or IIA, $R^{11}$ is fluoro. In certain embodiments, $R^{11}$ is iodo.

In one embodiment of the compounds of Formula II or IIA, $R^{11}$ is —OH, —O-$L^1$-$R^{17}$, —O-$L^1$-$R^{18}$, —O-$L^1$-$R^{19}$ or —O-$L^1$-$CHR^{17}R^{18}$. In one embodiment of the compounds of Formula I or IIA I, $R^{11}$ is —SH, —S-$L^1$-$R^{17}$, —S-$L^1$-$R^{18}$, —S-$L^1$-$R^{19}$ or —S-$L^1$-$CHR^{17}R^{18}$. In one embodiment of the compounds of Formula II or IIA, $R^{11}$ is —$NH_2$, —$NR^{16}$-$L^1$-$R^{17}$, —$NR^{16}$-$L^1$-$R^{19}$ or —$NR^{16}$-$L^1$-$CHR^{17}R^{18}$. In one embodiment of the compounds of Formula II or IIA, $R^{11}$ is —$S(O)_2N(R^{16})_2$.

In one embodiment of the compounds of Formula II or IIA, $R^{11}$ is —Cl, —Br, —I, —$OC(O)CH_2CH_3$, —$OC(O)CH_2Ph$, —$OC(O)OCH_2CH_3$, —$OC(O)OCH_2Ph$, —$OC(O)NH(CH(CH_3)Ph)$, —$OC(NPh)NHCH_2CH_3$, —$OC(O)NHCH_2Ph$, —$NH_2$, —$NHC(O)C(CH_3)_3$, —$NHC(O)CF_3$, —$NHC(O)CH_2Ph$, —$NHC(O)OCH_2Ph$, —$NHC(O)NH(CH(CH_3)Ph)$, —SH, —$SC(O)OCH_2Ph$, —$SC(O)NH(CH(CH_3)Ph)$, —$SC(O)CH_2CH_2OP(O)(OH)_2$, —$OC(O)CH_2CH_2CH(NH_2)(CO_2H)$, —$O$-($2$-OH—$C_6H_3$)$CH_2CH(NH_2)(CO_2H)$ or —$NHC(O)CH_2CH_2CH(NH_2)(CO_2H)$.

In one embodiment of the compounds of Formula II or IIA, $R^{12}$ is hydrogen.

In one embodiment of the compounds of Formula II or IIA, $R^{12}$ is —$CH_2CH_3$, —$CH_2CHCH_2$, —$CH_2Ph$, —$C(O)O(CH_2)_2N(CH_3)_2$ or —$C(O)CH_2(CH_2)_2SO_2N(CH_3)_2$.

In one embodiment of the compounds of Formula II or IIA, $R^{13}$ is hydrogen.

In one embodiment of the compounds of Formula II or IIA, $R^{13}$ is halo. In certain embodiments of the compounds of Formula II or IIA, $R^{13}$ is bromo. In certain embodiments of the compounds of Formula II or IIA, $R^{13}$ is fluoro.

In one embodiment of the compounds of Formula II or IIA, $R^{13}$ is —$OCH_3$, —$OCH_2CH_3$, —$OCH_2Ph$ or —CN.

In some embodiments of the compounds of Formula II or IIA, the compound is selected from any one of the compounds set forth below in Table 1:

TABLE 1

| No. | $R^{11}$ | $R^{12}$ | $R^{13}$ | ------ |
|---|---|---|---|---|
| 1 | Cl | H | H | double bond |
| 2 | Br | H | H | double bond |
| 3 | I | H | H | double bond |
| 4 | —$OC(O)CH_2CH_3$ | H | H | double bond |
| 5 | —$OC(O)CH_2Ph$ | H | H | double bond |
| 6 | —$OC(O)OCH_2CH_3$ | H | H | double bond |
| 7 | —$OC(O)OCH_2Ph$ | H | H | double bond |
| 8 | —$OC(O)NH(CH(CH_3)Ph)$ | H | H | double bond |
| 9 | —$OC(NPh)NHCH_2CH_3$ | H | H | double bond |
| 10 | —$OC(O)NHCH_2Ph$ | H | H | double bond |
| 11 | —$NH_2$ | H | H | double bond |
| 12 | —$NHC(O)C(CH_3)_3$ | H | H | double bond |
| 13 | —$NHC(O)CF_3$ | H | H | double bond |
| 14 | —$NHC(O)CH_2Ph$ | H | H | double bond |
| 15 | —$NHC(O)OCH_2Ph$ | H | H | double bond |
| 16 | —$NHC(O)NH(CH(CH_3)Ph)$ | H | H | double bond |
| 17 | —SH | H | H | double bond |
| 18 | —$SC(O)OCH_2Ph$ | H | H | double bond |
| 19 | —$SC(O)NH(CH(CH_3)Ph)$ | H | H | double bond |
| 20 | —$SC(O)CH_2CH_2OP(O)(OH)_2$ | H | H | double bond |
| 21 | —$OC(O)CH_2CH_2CH(NH_2)(CO_2H)$ | H | H | double bond |

TABLE 1-continued

| No. | $R^{11}$ | $R^{12}$ | $R^{13}$ | ------ |
|---|---|---|---|---|
| 22 | —O—(2-OH—$C_6H_3$)$CH_2CH(NH_2)(CO_2H)$ | H | H | double bond |
| 23 | —NHC(O)$CH_2CH_2CH(NH_2)(CO_2H)$ | H | H | double bond |
| 24 | —OH | H | H | single bond |
| 25 | Cl | H | H | single bond |
| 26 | Br | H | H | single bond |
| 27 | I | H | H | single bond |
| 28 | —OC(O)$CH_2CH_3$ | H | H | single bond |
| 29 | —OC(O)$OCH_2$Ph | H | H | single bond |
| 30 | —OC(O)NH(CH($CH_3$)Ph) | H | H | single bond |
| 31 | —OC(O)$NHCH_2$Ph | H | H | single bond |
| 32 | —$NH_2$ | H | H | single bond |
| 33 | —NHC(O)C($CH_3$)$_3$ | H | H | single bond |
| 34 | —NHC(O)NH(CH($CH_3$)Ph) | H | H | single bond |
| 35 | —SH | H | H | single bond |
| 36 | —SC(O)$OCH_2$Ph | H | H | single bond |
| 37 | —OH | —$CH_2CH_3$ | H | double bond |
| 38 | —OH | —$CH_2CHCH_2$ | H | double bond |
| 39 | —OH | —$CH_2$Ph | H | double bond |
| 40 | —OH | —C(O)O($CH_2$)$_2$N($CH_3$)$_2$ | H | double bond |
| 41 | —OH | —C(O)$CH_2$($CH_2$)$_2$$SO_2$N($CH_3$)$_2$ | H | double bond |
| 42 | —OH | H | —$OCH_2CH_3$ | double bond |
| 43 | —OH | H | —$OCH_2$Ph | double bond |
| 44 | —OH | H | —$CF_3$ | double bond |
| 45 | —OH | H | —OH | double bond |
| 46 | —OH | H | —CN | double bond | or a pharmaceutically acceptable salt thereof.

In certain embodiments, the compound of Formula I, IA, II, or IIA is the hydrochloride salt. In another embodiment, the compound of Formula I, IA, II, or IIA is the hydrobromide salt. In another embodiment, the compound of Formula I, IA, II, or IIA is the phosphate salt. In another embodiment, the compound of Formula I, IA, II, or IIA is the sulfate salt.

3. METHODS OF USE

Treatment of Pain

In one of its method aspect, the present invention is directed to a method for treating a pain in a patient which method comprises administering to said patient a compound of this invention or a pharmaceutically acceptable salt thereof or a pharmaceutical composition comprising a compound of this invention and a pharmaceutically acceptable excipient. The pain can be any type of pain including, but not limited to neuropathic or nociceptive pain, and various types thereof including somatic, visceral and phantom pain.

Treatment of Addiction

In another of its method aspect, the present invention is directed to a method for treating addiction in a patient which method comprises administering to said patient a compound of this invention or a pharmaceutically acceptable salt thereof or a composition comprising a compound of this invention and a pharmaceutically acceptable excipient.

In certain embodiments, the treatment of addiction in a patient comprises alleviating the symptoms associated withdrawal from drug dependency. Such symptoms include nausea, vomiting, anxiety, abdominal cramps, muscle pain, chills and headache. In addition, it is contemplated that treatment with a compound of this invention decreases the drug cravings normally experienced by addicts after cessation of the self administration of the abused substance. It is contemplated that the compositions disclosed herein are especially useful in the treatment of addiction to narcotics such as heroin and methadone. However, it is also useful in treating patients addicted to cocaine, alcohol, amphetamines and combinations of these drugs.

The invention is also directed to a method for treating drug addiction (involving drug dependency or drug abuse) during withdrawal therapy by administering a compound of this invention to a patient at a dosage sufficient to reduce or eliminate one or more symptoms associated withdrawal. Such symptoms include nausea, vomiting, anxiety, abdominal cramps, muscle pain, chills and headache. In addition, treatment with a compound of this invention is contemplated to decrease the drug cravings normally experienced by addicts after cessation of the self administration of the abused substance, for example, narcotics such as heroin and methadone. However, compounds of this invention are contemplated to be also useful in treating patients addicted to cocaine, alcohol, amphetamines and combinations of these drugs. Compounds of this invention may be administered to patients suffering from drug dependence or abuse in conjunction with an opioid antagonist such as naloxone, naltrexone or nalorphine, for example, at a concentration of between 0.15 mg and 0.5 mg for each mg of the compound of this invention administered.

Combination Therapy

Compounds of this invention maybe used alone or in combination with other compounds to treat pain and/or addiction. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

In some embodiments, a compound of this invention can be used as an adjunct to conventional drug withdrawal therapy, specifically providing for the administration of a compound of this invention with one or more opioid antagonists.

4. COMPOSITIONS

In another aspect, this invention is also directed to pharmaceutical compositions comprising a pharmaceutically acceptable excipient and a compound of this invention or mixtures of one or more of such compounds.

Although compositions suitable for oral, intravenous or intraarterial delivery will probably be used most frequently, other routes that may be used include peroral, pulmonary, rectal, nasal, vaginal, lingual, intramuscular, intraperitoneal, intracutaneous and subcutaneous routes. In addition, it is contemplated that the composition can be administered transdermally in which drug is applied as part of a cream, gel, or patch (for examples of transdermal formulations, see U.S. Pat. Nos. 4,806,341; 5,149,538; and 4,626,539). Other dosage forms include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980). Intranasal administration is an effective method for delivering a therapeutic agent directly to the respiratory tract, where the therapeutic agent may be quickly absorbed.

The compositions are comprised of in general, a compound of this invention or a mixture thereof in combination with at least one pharmaceutically acceptable excipient. Acceptable excipients are non-toxic, aid administration, and do not adversely affect the therapeutic benefit of the compound of this invention. Such excipients may be any solid, liquid, semisolid or, in the case of an aerosol composition, gaseous excipient that is generally available to one of skill in the art. Pharmaceutical compositions in accordance with the invention are prepared by conventional means using methods known in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing noribogaine may be prepared using conventional techniques that may include sterile isotonic saline, water, 1,3-butanediol, ethanol, 1,2-propylene glycol, polyglycols mixed with water, Ringer's solution, etc.

The amount of the compound in a formulation can vary within the full range employed by those skilled in the art. Typically, the formulation will contain, on a weight percent (wt %) basis, from about 0.01 to 99.99 wt % of a compound of this invention based on the total formulation, with the balance being one or more suitable pharmaceutical excipients. Preferably, the compound is present at a level of about 1 to 80 wt %. In a liquid composition, a compound of this invention should generally be present in such compositions at a concentration of between about 0.1 and 20 mg/ml. When either naloxone or naltrexone is combined with a compound of this invention, they should be present at 0.05 to 0.5 mg for each mg of the compound of this invention.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Generally, the compound of this invention is administered in an effective amount. It is contemplated that the dosage required for treating pain or addition, or a combination thereof may differ according to the condition(s) being treated, however, the dosing regimen can be readily determined by the attending clinician based on the desired treatment. It is contemplated that generally, the dosage of a compound of this invention administered to a patient may be from about 0.01 to about 1000 mg per kg of body weight per day (mg/kg/day), or from 0.05 to 500 mg/kg/day, preferably, from about 0.1 to about 100 mg/kg/day, more preferably from about 0.5 to 50 mg/kg/day. For example, for administration to a 70 kg person, the dosage range would preferably be about 35 to 700 mg per day.

In addition to the methods discussed above, the present invention is directed to a pharmaceutical composition, preferably in unit dose form, comprising a compound of this invention. When administered to a patient, one or more unit doses provide an amount of a compound of this invention effective to treat pain and/or addition.

The amount of the composition administered will depend on a number of factors, including but not limited to the desired final concentration of the compound, the pharmacokinetic and pharmacodynamic properties of the compound, the size, age, and physiological profile of the patient, and the like. The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

Determination of dosages is well within the empiric knowledge of persons skilled in the art; nonetheless, it can be appreciated that estimates of final dosages can be made by approximating the concentration of compound necessary to achieve a desired therapeutic activity, such as treatment of pain and/or addiction. Extrapolation to a specified mammalian dosage range, or more particularly a human dosage range is well within the skill of the practitioner.

In some embodiments, compositions are administered in one dosing of a single formulation and in other embodiments, compositions are administered in multiple dosing of a single formulation within a specified time period. In some embodiments, the time period is between about 3 hours to about 6 hours. In other embodiments, the time period is between about 6 hours and 12 hours. In additional embodiments, the time period is between about 12 hours and 24 hours. In yet further embodiments, the time period is between about 24 hours and 48 hours. The administration of separate formulations can be simultaneous or staged throughout a specified time period, such that all ingredients are administered within the specified time period.

The following are examples of the compositions of this invention.

Example 1

Tablet Formulation

The following ingredients are mixed intimately and pressed into single scored tablets.

| Ingredient | Quantity per tablet, mg |
|---|---|
| Compound of Formula I | 40 |
| Cornstarch | 50 |
| Croscarmellose sodium | 25 |
| Lactose | 120 |
| Magnesium stearate | 5 |

Example 2

Capsule Formulation

The following ingredients are mixed intimately and loaded into a hard-shell gelatin capsule.

| Ingredient | Quantity per tablet, mg |
|---|---|
| Compound of Formula I | 20 |
| Lactose, spray-dried | 148 |
| Magnesium stearate | 2 |

Example 4

Suspension Formulation

The following ingredients are mixed to form a suspension for oral administration (q.s.=sufficient amount).

| Ingredient | Amount |
|---|---|
| Compound of Formula I | 1.0 g |
| Fumaric acid | 0.5 g |
| Sodium chloride | 2.0 g |
| Methyl paraben | 0.15 g |
| Propyl paraben | 0.05 g |
| Granulated sugar | 25.0 g |
| Sorbitol (70% solution) | 13.0 g |
| Veegum K (Vanderbilt Co) | 1.0 g |
| flavoring | 0.035 mL |
| colorings | 0.5 mg |
| distilled water | q.s. to 100 mL |

Example 3

Injectable Formulation

The following ingredients are mixed to form an injectable formulation.

| Ingredient | Quantity per tablet, mg |
|---|---|
| Compound of Formula I | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Example 4

Suppositor Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Quantity per tablet, mg |
|---|---|
| Compound of Formula I | 500 mg |
| Witepsol ® H-15 | balance |

5. SYNTHETIC METHODS

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Still further, some of the compounds defined herein include vinyl groups which can exist in cis, trans or a mixture of cis and trans forms. All combinations of these forms are within the scope of this invention.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1 15 (John Wiley and Sons, 1991), Rodd's Chemistry of Carbon Compounds, Volumes 1 5 and Supplementals (Elsevier Science Publishers, 1989), Organic Reactions, Volumes 1 40 (John Wiley and Sons, 1991), March's Advanced Organic Chemistry, (John Wiley and Sons, 4.sup.th Edition), and Larock's Comprehensive Organic Transformations (VCH Publishers Inc., 1989).

Compounds of this invention may be prepared using the starting material Compound 1.1, which may be prepared according to Scheme 2, according to known procedures, such as those described in Bornmann, et al., *J. Org. Chem.*, 57:1752 (1992) and U.S. Pat. No. 6,211,360, which are hereby incorporated by reference in their entirety. Scheme 1 shows an exemplary general process for prepare compounds of this invention. The starting materials for the following reactions are generally known compounds or can be prepared by known procedures.

Scheme 1

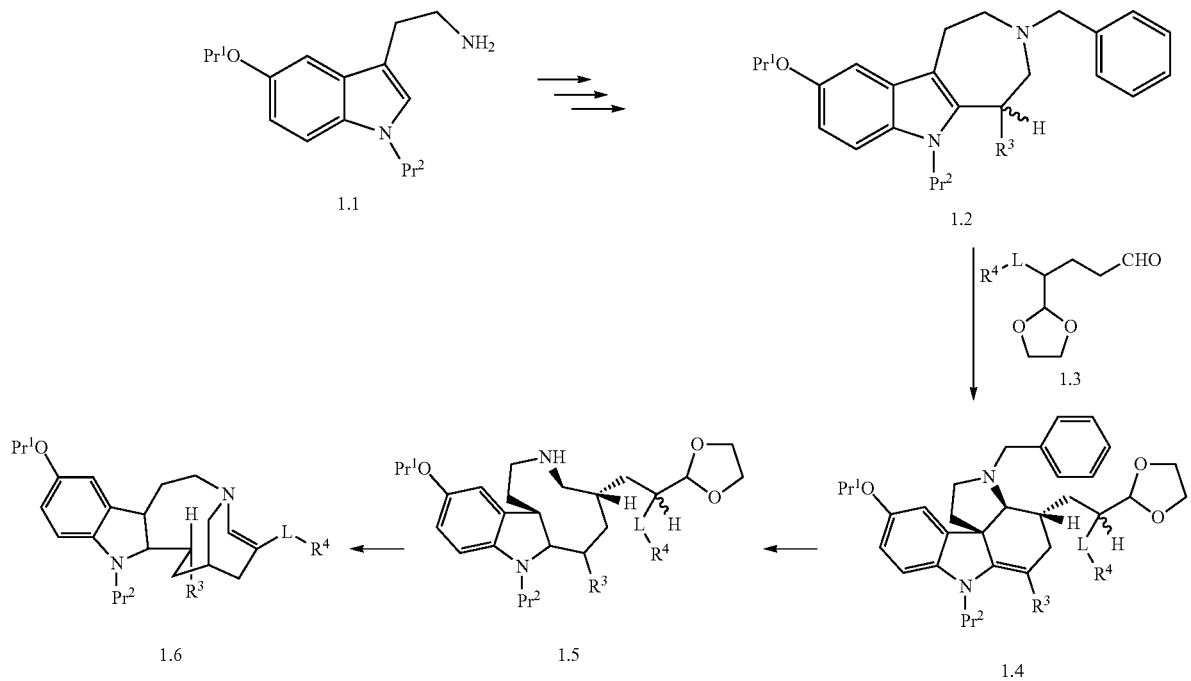

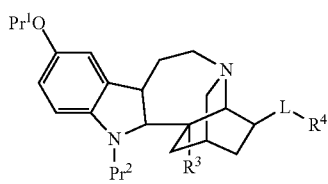 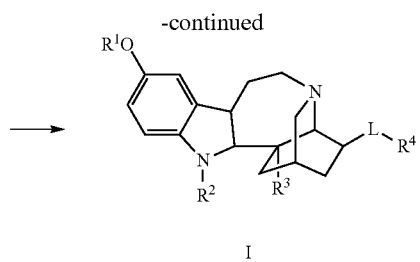

1.7    I

Scheme 1 shows an exemplifying procedure to prepare compounds of Formula I, wherein $R^2$, $R^3$, L and $R^4$ are as defined herein. Compound 1.1, wherein $Pr^1$ is $R^1$ as defined herein or a hydroxy protecting group, and $Pr^2$ is $R^2$ as defined herein or a protecting group for the indole nitrogen, is converted to Compound 1.2 using the procedure described in Kuehne, et al. *J. Org. Chem.* 50:919 (1985). Hydroxyl protecting groups include a hydrolysable group as defined for Formula I, such as —C(O)R, wherein R is as defined herein, and other hydroxyl protecting groups known in the art, such as a benzyl (Bn) group, 2,4-dichlorobenzyl (DCB), methoxymethyl (MOM), tetrahydropyranyl (THP), acyl (such as acetyl (Ac)) or a silyl group, etc. Other suitable hydroxy protecting groups are known in the art. Protecting groups for the indole nitrogen include arylsulfonyl derivatives (e.g. tosyl (Ts)), carbamates (e.g. fluorenylmethyloxycarbonyl (Fmoc) and tert-butyloxycarbonyl (t-BOC), trialkylsilyl groups (e.g. triisopropylsilyl), N,O-acetals (e.g. (trimethylsilyl)ethoxymethyl ether (SEM)) and certain substituted alkyl groups (e.g. benzyl). The need to protect and the types of protecting groups used for the hydroxy and/or the indole nitrogen will depend on the exact reaction conditions and reagents used in subsequent steps, which would be generally known in the art. When $Pr^1$ is $R^1$ and/or $Pr^2$ is $R^2$, they can be retained as part of the final compounds, or may be converted to other groups as defined in Formula I by methods generally known in the art. When $Pr^1$ and/or $Pr^2$ are other protecting groups, they can be removed under proper deprotection conditions to provide the free hydroxy group and/or free indole nitrogen, which may be further converted to the $R^1$ and/or $R^2$ groups as defined in Formula I.

Compound 1.2 may react with Compound 1.3 to give Compound 1.4 in dry toluene under reflux conditions, and preferably with a Dean-Stark trap with molecular sieves. Compound 1.3 can be prepared by using methods described in U.S. Pat. No. 6,211,360, which is incorporated by reference in its entirety.

Alternatively, Compound 1.2 may react with Compound 1.3 to give a condensation product in an organic solvent, such as alcohol solvents, such as methanol, ethanol, isopropanol, and n-butanol; ester-containing solvents, such as ethyl acetate and isopropyl acetate; ether solvents, such as tetrahydrofuran, diglyme, and dioxane; chlorinate hydrocarbons, such as methylene chloride, chloroform, and carbon tetrachloride; aromatic hydrocarbons, such as benzene, toluene, and xylene; acetonitrile; pyridine; and dimethylformamide. The reaction may proceed under room temperature or under heated conditions, such refluxing conditions. After the condensation reaction, the condensation product is treated in a suitable solvent with an equivalent amount of an appropriate arylalkyl containing a good leaving group, such as an arylalkyl tosylate, an arylalkyl mesylate, or an arylalkyl halide, such as benzyl bromide, for 0.5 to 72 hours, for example, 16 hours, at 50° C. to 120° C., which may be at the reflux temperature of the solvent. Suitable solvents include lower alkanes, such as pentane, hexane, or petroleum ether; aromatic hydrocarbon solvents, such as benzene, toluene, and xylene; alcohols, such as methanol, ethanol, isopropanol, and n-butanol; and ether solvents, such as diethyl ether, diglyme, or tetrahydrofuran.

Treatment of the above product, with an organic-soluble Lewis base, such as triethylamine, produces a transient enamine acrylate of the formula:

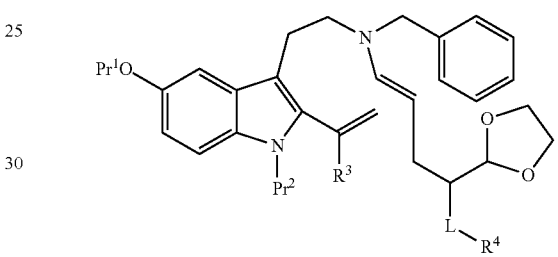

This reaction can proceed in an organic solvent, including alcohol solvents, such as methanol, ethanol, isopropanol, and n-butanol; ketone solvents, such as acetone, methyl ethyl ketone, and cyclopentanone; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; and dimethylformamide. This reaction can be conducted at any temperature from room temperature to the boiling point of the solvent, for example, from 50° C. to 70° C. for, for example, from 1 to 10 hours. The transient enamine acrylate spontaneously cyclizes to give Compound 1.4.

Compound 1.4 undergoes reduction with a reducing agent, such as $NaBH_4$, in the presence of acetic acid, under heating conditions, for example, at a temperature of between 80° C. and 110° C., or between 85° C. and 95° C., followed by catalytic hydrogenation in the presence of a catalyst, such as palladium, in a solvent, such as methanol, to provide Compound 1.5.

Hydrolysis of Compound 1.5 under acidic conditions, for example, with glacial acetic acid and/or hydrochloric acid in a solvent, such as MeOH gives Compound 1.6, which undergoes cyclization to give Compound 1.7 in a dry solvent under heating conditions, for example, in dry toluene at 130° C.

Finally, $Pr^1$ and/or $Pr^2$ may be removed under suitable deprotection conditions to provide compounds where $R^1$ and/or $R^2$ are hydrogen. One or both of these hydrogen atoms may be substituted by a desired $R^1$ and/or $R^2$ by reaction with $R^1Lg$ and/or $R^2Lg$, wherein Lg is a leaving group, such as a halo group (e.g., chloro, bromo and iodo), sulfonate esters, such as para-toluenesulfonate or tosylate (OTs), hydroxy or alkoxy group. Further manipulations of the $R^1$, $R^2$, $R^3$ and/or $R^4$ to provide other embodiments of this invention are apparent to a person skilled in the art.

In Scheme 2, Compound 2.1 (5-hydroxyindole-3-acetic acid, which is commercially available, for example, from Sigma-Aldrich Corp.) may be protected to give Compound 2.2, wherein $Pr^1$ and $Pr^2$ are as defined above. Compound 2.2 is reduced to the corresponding alcohol Compound 2.3, using a reducing agent, such as lithium aluminumhydride. Reduction of Compound 2.2 to Compound 2.3 may optionally conducted via an intermediate aldehyde compound. The hydroxy group of Compound 2.3 is converted to a leaving group $Lg^2$, such as a halo group (e.g., chloro, bromo and iodo), sulfonate esters, such as para-toluenesulfonate or tosylate (OTs), to give Compound 2.4. Compound 2.4 can react with ammonium to give Compound 1.1 or with a protected ammonium compound, such as NH(t-Boc)$_2$ to give Compound 1.1 after deprotection of the protecting group. Other known methods of converting the acid group (—C(O)OH) to an methyl amino group (—CH$_2$NH$_2$) can also be used.

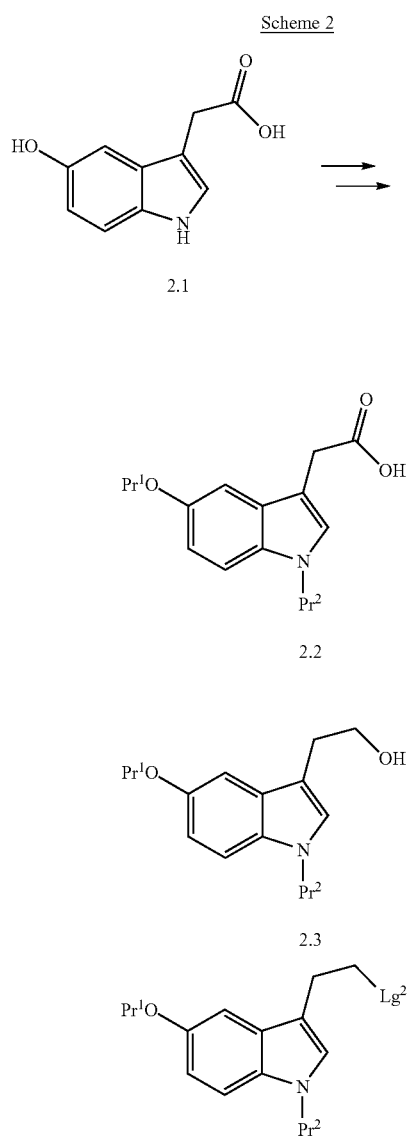

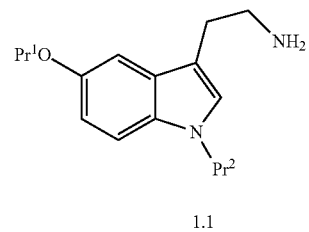

By using commercially available 5-bromoindole-3-acetic acid and following Scheme 2, the bromo compound corresponding to Compound 1.1 can be prepared, which can be used to replace Compound 1.1 in Scheme 1 to prepare compounds of this invention wherein R is bromo. The bromo atom can be converted to other R groups as defined for Formula I using procedures known in the art. For example, reaction with a suitable agent, such as haloalkyl, haloalkenyl, or haloalkynyl, optionally in the presence of a copper (I) or palladium catalyst and/or a base, such as triethylamine, would give compounds where R is alkyl (when using haloalkenyl or haloalkynyl, the double bond or triple bond can be reduced by hydrogenation).

Scheme 3 shows an example of preparing an intermediate Compound 3.5, which may be used in Scheme 1 to replace Compound 1.1 to prepare compounds of this invention where R is chloro. In Scheme 3, Compound 3.1 (5-chloroindole-3-carboxaldehyde, which is commercially available, for example, from Sigma-Aldrich Corp.) is protected with $Pr^2$ to give Compound 3.2. Compound 3.2 may react with a Wittig agent, e.g. Ph$_3$PCH$_3$$^+$Br$^-$, to give Compound 3.3. Compound 3.3 is converted to Compound 3.4, wherein Halo is a halo such as Br or Cl, by reacting with, for example, hydrogen bromide (HBr). Compound 3.4 can react with ammonium to give Compound 3.5 or with a protected ammonium compound, such as NH(t-Boc)$_2$ to give Compound 3.5 after deprotection of the protecting group. Other known methods of converting the acid group (—C(O)OH) to an methyl amino group (—CH$_2$NH$_2$) can also be used.

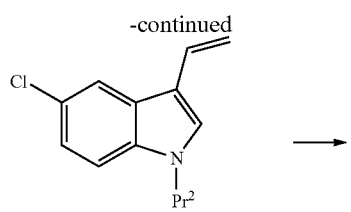

3.3

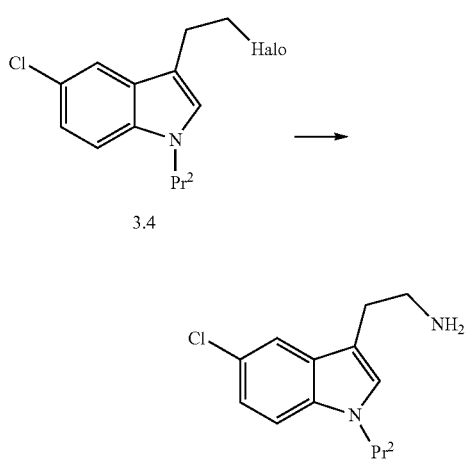

3.4

3.5

Further compounds of the present invention can be prepared according to Scheme 4 from noribogaine derivatives (as can be prepared by the synthesis disclosed above, for example) by methods known to one of skill in the art. A skilled artisan would appreciate that the reactivity of the hydroxy group and the indole nitrogen is different so that selectivity can be achieved by selecting suitable reagents and suitable reaction conditions for one of them to react but leaving the other intact to form the desired product. For example, the hydroxy group is expected to selectively react with a carboxylic acid in the presence of triphenylphosphine ($Ph_3P$) and diethyl azodicarboxylate (DEAD) to give Compound 4.1 and Compound 4.3 where L is —C(O)alkylene or —C(O)arylene. Thus, as shown in Scheme 4, noribogaine derivatives can react with appropriately protected compounds of formula LG-$R^{30}$ where $R^{30}$ is -$L^1$-$R^{17}$, -$L^1$-$R^{18}$, -$L^1$-$R^{19}$ or -$L^1$-$CHR^{17}R^{18}$, LG is a leaving group such as hydroxy, alkoxy, halo, etc., to give Compound 4.2, which may further react with LG-$R^{12}$ to form Compound 4.3. In other embodiments (i.e. when $R^{30}$ is H), the C12-phenol, thiol, or amino group is protected by reaction with a suitable protecting group, PG-LG, where LG is a leaving group such as defined above, such that the indole nitrogen is selectively derivatized with $R^{12}$. Suitable protecting groups are well known in the art (see T. W. Greene, P. G. M. Wuts, Protective Groups in Organic Synthesis, 4$^{th}$ Edition, Wiley-Interscience, New York, 2006). In another alternative embodiment (i.e. when $R^{12}$ is H), the indole nitrogen is protected with a suitable protecting group, PG (see Greene et al., supra), such that the C12-phenol, thiol, or amino group is free to be derivatized with $R^{30}$.

Scheme 4

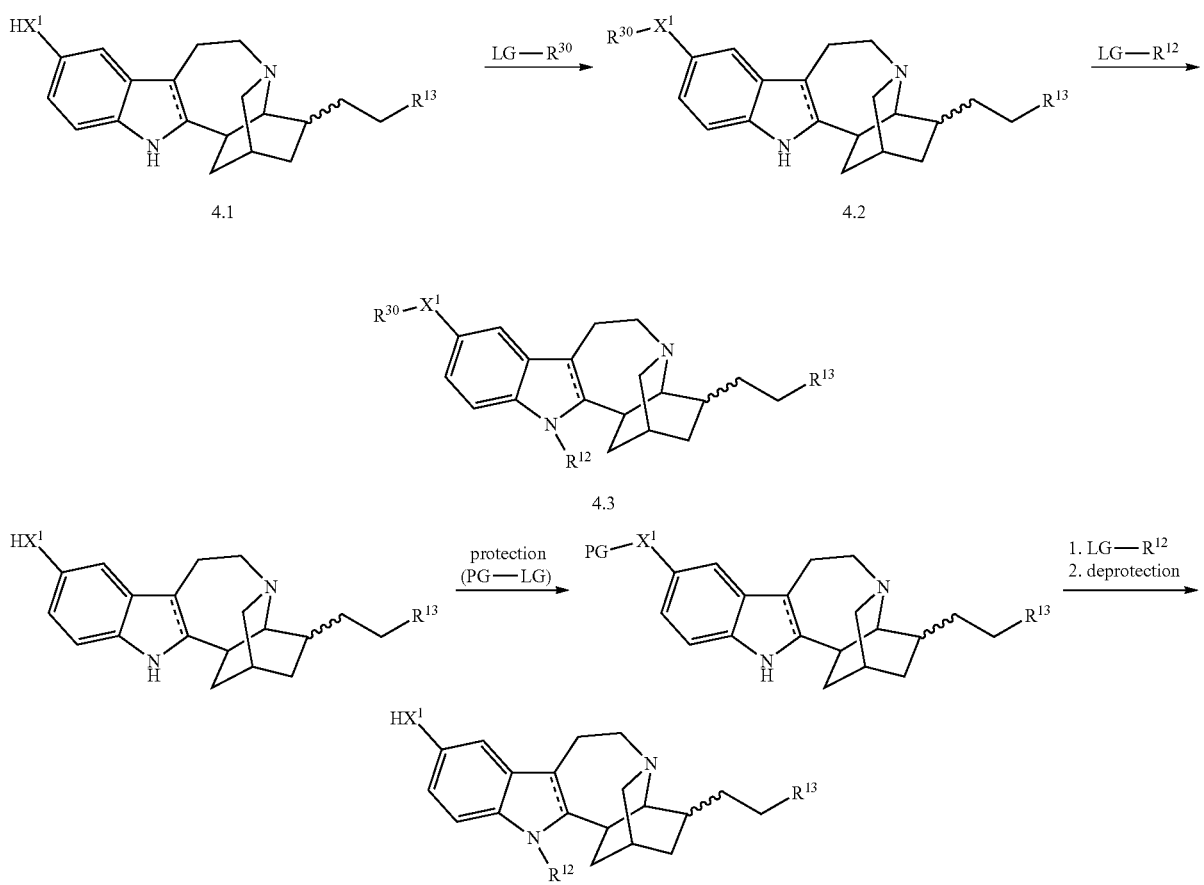

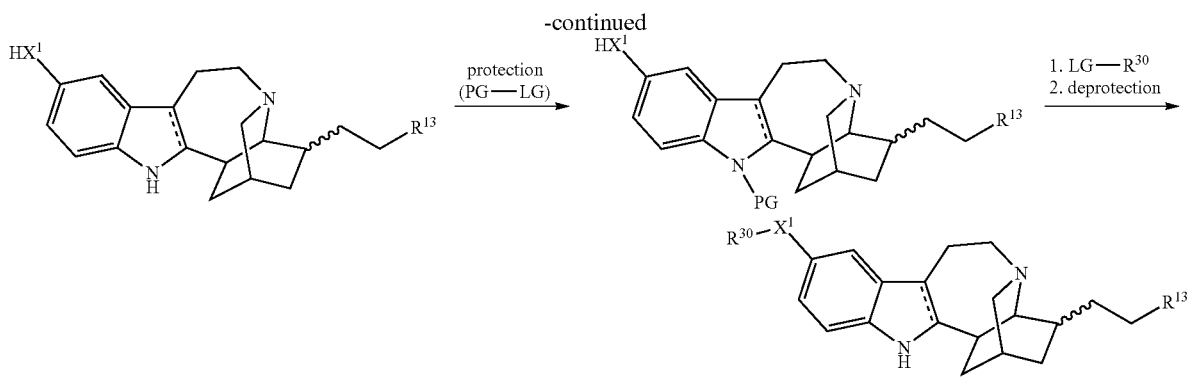

Alternatively, as shown in Scheme 5, certain compounds of this invention may be prepared by reacting ibogaine with LG-$R^{12}$ to give Compound 5.1. Compound 5.1 can be demethylated by methods known in the art, such as reaction with boron tribromide/methylene chloride at room temperature to give Compound 5.2, which may further react with LG-$R^{30}$ to give Compound 5.3.

Scheme 5

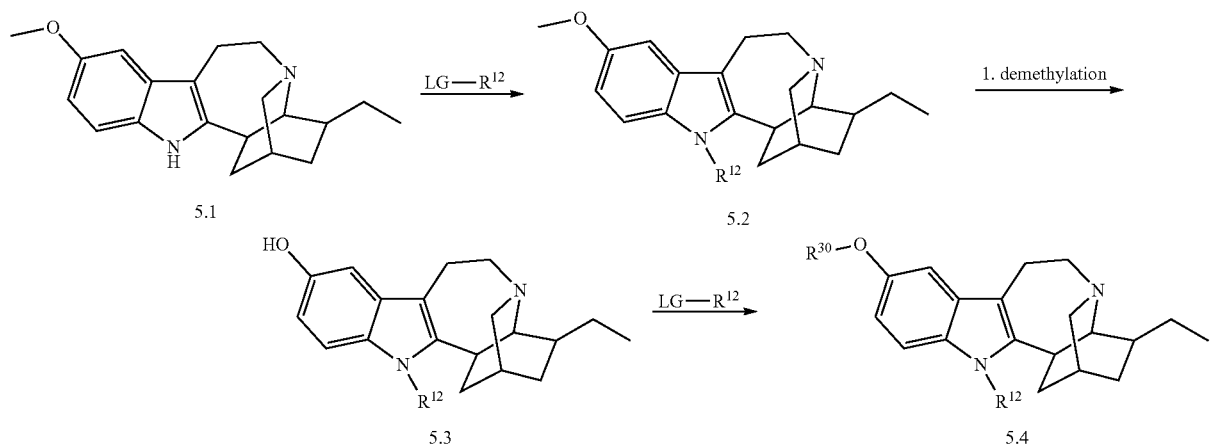

It will be apparent to those skilled in the art that many modifications of the above exemplifying methods, both to materials and methods, may be practiced without departing from the scope of the current invention.

What is claimed is:

1. A compound of Formula IA or Formula IB, or a pharmaceutically acceptable salt of each thereof:

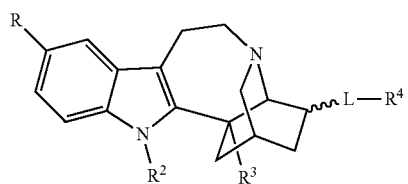

IA

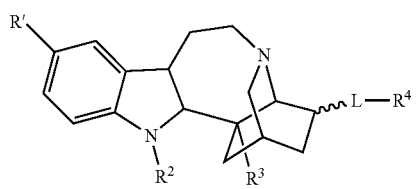

IB wherein

R is $OR^1$ or $C_1$-$C_{12}$ alkyl optionally substituted with 1 to 5 $R^9$;

$R^1$ is selected from the group consisting of hydrogen, —C(O)OX and —C(O)N(Y)$_2$ where X is $C_1$-$C_6$ alkyl optionally substituted with 1 to 5 $R^9$, and each Y is independently selected from the group consisting of hydrogen, $C_1$-$C_6$ alkyl optionally substituted with 1 to 5 $R^9$, $C_6$-$C_{14}$ aryl optionally substituted with 1 to 5 $R^9$, $C_3$-$C_{10}$ cycloalkyl optionally substituted with 1 to 5 $R^9$, $C_1$-$C_{10}$heteroaryl having 1 to 4 heteroatoms and which is optionally substituted with 1 to 5 $R^9$, $C_1$-$C_{10}$heterocyclic having 1 to 4 heteroatoms and which is optionally substituted with 1 to 5 $R^9$, or where each Y, together with the nitrogen atom bound thereto form either a $C_1$-$C_6$ heterocyclic having 1 to 4 heteroatoms and which is optionally substituted with 1 to 5 $R^9$, or a $C_1$-$C_6$heteroaryl having 1 to 4 heteroatoms and which is optionally substituted with 1 to 5 $R^9$;

$R^1$ is halo, $OR^{20}$, or $C_1$-$C_{12}$ alkyl optionally substituted with 1 to 5 $R^9$;

$R^{20}$ is selected from the group consisting of hydrogen, —C(O)X, —C(O)OX and —C(O)N(Y)$_2$ where X and Y are defined as above;

$R^2$ is hydrogen;

$R^3$ is selected from the group consisting of hydrogen, —(CH$_2$)$_m$OR$^7$, —CR$^6$(OH)R$^7$, —(CH$_2$)$_m$CN, —(CH$_2$)$_m$ COR$^7$, —(CH$_2$)$_m$CO$_2$R$^7$, —(CH$_2$)$_m$C(O)NR$^6$R$^7$, —(CH$_2$)$_m$C(O)NR$^6$NR$^7$R$^7$, —(CH$_2$)$_m$C(O)NR$^6$NR$^7$C(O)R$^8$, and —(CH$_2$)$_m$NR$^6$R$^7$;

m is 0, 1, or 2;

L is a bond or $C_1$-$C_{12}$ alkylene;

$R^4$ is selected from the group consisting of, $C_1$-$C_{12}$ alkyl substituted with 1 to 5 $R^9$, $C_2$-$C_{12}$ alkenyl substituted with 1 to 5 $R^9$, —X$^2$—R$^6$, —(X$^2$—Y$^2$)$_n$—X$^2$—R$^6$, —SO$_2$NR$^6$R$^7$, —O—C(O)R$^8$, —C(O)OR$^7$, —C(O)NR$^6$R$^7$, —NR$^6$R$^7$, —NHC(O)R$^8$, and —NR$^6$C(O)R$^8$;

$X^2$ is selected from the group consisting of O and S;

$Y^2$ is $C_1$-$C_4$ alkylene or $C_6$-$C_{10}$ arylene, or a combination thereof;

n is 1, 2, or 3;

$R^6$ and $R^7$ are each independently selected from the group consisting of hydrogen, $C_1$-$C_{12}$ alkyl optionally substituted with 1 to 5 $R^9$, $C_1$-$C_6$ heterocycle having 1 to 4 heteroatoms and which is optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$heteroaryl having 1 to 4 heteroatoms optionally substituted with 1 to 5 $R^9$;

$R^8$ is selected from the group consisting of $C_1$-$C_{12}$ alkyl optionally substituted with 1 to 5 $R^9$, $C_1$-$C_6$ heterocycle having 1 to 4 heteroatoms optionally substituted with 1 to 5 $R^9$, $C_3$-$C_{10}$ cycloalkyl optionally substituted with 1 to 5 $R^9$, $C_6$-$C_{10}$ aryl optionally substituted with 1 to 5 $R^9$ and $C_1$-$C_6$ heteroaryl having 1 to 4 heteroatoms optionally substituted with 1 to 5 $R^9$;

$R^9$ is selected from the group consisting of $C_1$-$C_4$ alkyl, phenyl, halo, —OR$^{10}$, —CN, —COR$^{10}$, —CO$_2$R$^{10}$, —C(O)NHR$^{10}$, —NR$^{10}$R$^{10}$, —C(O)NR$^{10}$R$^{10}$, —C(O)NHNHR$^{10}$, —C(O)NR$^{10}$NHR$^{10}$, —C(O)NR$^{10}$NR$^{10}$R$^{10}$, —C(O)NHNR$^{10}$C(O)R$^{10}$, —C(O)NHNHC(O)R$^{10}$, —SO$_2$NR$^{10}$R$^{10}$, —C(O)NR$^{10}$NR$^{10}$C(O)R$^{10}$, and —C(O)NR$^{10}$NHC(O)R$^{10}$; and $R^{10}$ is $C_1$-$C_{12}$ alkyl;

provided that:

for the compound of Formula IA, when R is —OH or $C_1$-$C_{12}$ alkyl optionally substituted with 1 to 5 $R^9$, then $R^3$ is hydrogen; and for the compound of Formula IA, when $R^3$ is hydrogen, and -L-$R^4$ is ethyl, then R is not —OR$^1$.

2. A compound of Formula IIB or Formula IIC or a pharmaceutically acceptable salt of each thereof:

IIB

IIC wherein $R^{11}$ is —SH or —S(O)$_2$N(R$^{16}$)$_2$;

$R^{21}$ is halo, —OH, —SH, —NH$_2$, or —S(O)$_2$N(R$^{16}$)$_2$; and each $R^{16}$ is independently hydrogen or $C_1$-$C_{12}$ alkyl optionally substituted with from 1 to 3 halo.

3. The compound of claim 2, represented by Formula IID, or a pharmaceutically acceptable salt thereof:

IID

4. The compound of claim 2, represented by Formula IIE, or a pharmaceutically acceptable salt thereof:

IIE

5. The compound of claim 2 of Formula IIC, wherein $R^{21}$ is halo.

6. The compound of claim 2 of Formula IIC, wherein $R^{21}$ is —OH.

7. The compound of claim 2 of Formula IIB, wherein $R^{11}$ is —SH.

8. The compound of claim 2 of Formula IIC, wherein $R^{21}$ is —SH.

9. The compound of claim 2 of Formula IIC, wherein $R^{21}$ is —$NH_2$.

10. The compound of claim 2 of Formula IIB, wherein $R^{11}$ is —$S(O)_2N(R^{16})_2$.

11. The compound of claim 2 of Formula IIC, wherein $R^{21}$ is —$S(O)_2N(R^{16})_2$.

12. A compound of Formula IIF:

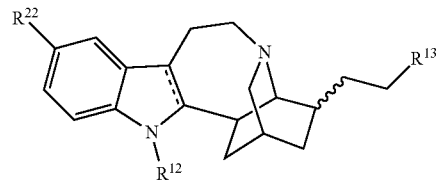

or a pharmaceutically acceptable salt thereof, wherein the compound is selected from the group consisting of compounds wherein $R^{22}$, $R^{12}$, $R^{13}$, and ====== are defined as follows:

| No. | $R^{22}$ | $R^{12}$ | $R^{13}$ | ====== |
|---|---|---|---|---|
| 6 | —OC(O)OCH$_2$CH$_3$ | H | H | double bond |
| 7 | —OC(O)OCH$_2$Ph | H | H | double bond |
| 8 | —OC(O)NH(CH(CH$_3$)Ph) | H | H | double bond |
| 9 | —OC(NPh)NHCH$_2$CH$_3$ | H | H | double bond |
| 10 | —OC(O)NHCH$_2$Ph | H | H | double bond |
| 12 | —NHC(O)C(CH$_3$)$_3$ | H | H | double bond |
| 13 | —NHC(O)CF$_3$ | H | H | double bond |
| 14 | —NHC(O)CH$_2$Ph | H | H | double bond |
| 15 | —NHC(O)OCH$_2$Ph | H | H | double bond |
| 16 | —NHC(O)NH(CH(CH$_3$)Ph) | H | H | double bond |
| 17 | —SH | H | H | double bond |
| 18 | —SC(O)OCH$_2$Ph | H | H | double bond |
| 19 | —SC(O)NH(CH(CH$_3$)Ph) | H | H | double bond |
| 20 | —SC(O)CH$_2$CH$_2$OP(O)(OH)$_2$ | H | H | double bond |
| 21 | —OC(O)CH$_2$CH$_2$CH(NH$_2$)(CO$_2$H) | H | H | double bond |
| 22 | —O—(2-OH—C$_6$H$_3$)CH$_2$CH(NH$_2$)(CO$_2$H) | H | H | double bond |
| 23 | —NHC(O)CH$_2$CH$_2$CH(NH$_2$)(CO$_2$H) | H | H | double bond |
| 24 | —OH | H | H | single bond |
| 25 | Cl | H | H | single bond |
| 26 | Br | H | H | single bond |
| 27 | I | H | H | single bond |
| 28 | —OC(O)CH$_2$CH$_3$ | H | H | single bond |
| 29 | —OC(O)OCH$_2$Ph | H | H | single bond |
| 30 | —OC(O)NH(CH(CH$_3$)Ph) | H | H | single bond |
| 31 | —OC(O)NHCH$_2$Ph | H | H | single bond |
| 32 | —NH$_2$ | H | H | single bond |
| 33 | —NHC(O)C(CH$_3$)$_3$ | H | H | single bond |
| 34 | —NHC(O)NH(CH(CH$_3$)Ph) | H | H | single bond |
| 35 | —SH | H | H | single bond |
| 36 | —SC(O)OCH$_2$Ph | H | H | single bond |
| 37 | —OH | —CH$_2$CH$_3$ | H | double bond |
| 38 | —OH | —CH$_2$CHCH$_2$ | H | double bond |
| 39 | —OH | —CH$_2$Ph | H | double bond |
| 40 | —OH | —C(O)O(CH$_2$)$_2$N(CH$_3$)$_2$ | H | double bond |
| 41 | —OH | —C(O)CH$_2$(CH$_2$)$_2$SO$_2$N(CH$_3$)$_2$ | H | double bond |
| 42 | —OH | H | —OCH$_2$CH$_3$ | double bond |
| 43 | —OH | H | —OCH$_2$Ph | double bond |
| 44 | —OH | H | —CF$_3$ | double bond |
| 45 | —OH | H | —OH | double bond |
| 46 | —OH | H | —CN | double bond. |

13. A composition comprising a compound of claim 1 and a pharmaceutically acceptable excipient.

14. A composition comprising a compound of claim 2 and a pharmaceutically acceptable excipient.

15. A composition comprising a compound of claim 12 and a pharmaceutically acceptable excipient.

* * * * *

UNITED STATES PATENT AND TRADEMARK OFFICE
CERTIFICATE OF CORRECTION

PATENT NO.       : 8,362,007 B1
APPLICATION NO.  : 13/104410
DATED            : January 29, 2013
INVENTOR(S)      : Deborah C. Mash Page 1 of 1

It is certified that error appears in the above-identified patent and that said Letters Patent is hereby corrected as shown below:

In the Specifications:
Column 2, line 41: delete "–$(CH_2)_m$ $OR^7$" and replace it with -- –$(CH_2)_m$ $COR^7$--

Column 3, line 44: delete "addition" and replace it with --addiction--

Column 17, line 38: delete "aspect" and replace it with --aspects--

Column 17, line 49: delete "aspect" and replace it with --aspects--

Column 20, line 52: delete "addition" and replace it with --addiction--

Column 21, line 2: delete "addition" and replace it with --addiction--

Column 24, line 34: delete "prepare" and replace it with --preparing--

Column 25, line 61: add --as-- after "such"

Column 28, line 44: delete "an" and replace it with --a--

In the Claims:
Column 32, line 67: insert a space after "$C_1$-$C_{10}$"

Column 33, line 2: insert a space after "$C_1$-$C_{10}$"

Column 33, line 9: insert a space after "$C_1$-$C_6$"

Column 33, line 27: remove "," after "of"

Column 33, line 46: insert a space after "$C_1$-$C_6$"

Signed and Sealed this
Twenty-third Day of April, 2013

Teresa Stanek Rea
*Acting Director of the United States Patent and Trademark Office*